United States Patent
Garsha et al.

(10) Patent No.: US 9,310,302 B2
(45) Date of Patent: Apr. 12, 2016

(54) MULTI-MODALITY CONTRAST AND BRIGHTFIELD CONTEXT RENDERING FOR ENHANCED PATHOLOGY DETERMINATION AND MULTI-ANALYTE DETECTION IN TISSUE

(75) Inventors: Karl Garsha, Sahuarita, AZ (US); Gary Pestano, Oro Valley, AZ (US); Michael Otter, Tucson, AZ (US); Alexandra Dea Nagy, Oro Valley, AZ (US); Ray B. Nagle, Tucson, AZ (US); Phillip Miller, Tucson, AZ (US); Jan Froehlich, Oro Valley, AZ (US); William Day, Tucson, AZ (US)

(73) Assignee: VENTANA MEDICAL SYSTEMS, INC., Tucson, AZ (US)

( * ) Notice: Subject to any disclaimer, the term of this patent is extended or adjusted under 35 U.S.C. 154(b) by 1001 days.

(21) Appl. No.: 13/499,959

(22) PCT Filed: Oct. 7, 2010

(86) PCT No.: PCT/US2010/051857
§ 371 (c)(1),
(2), (4) Date: Apr. 3, 2012

(87) PCT Pub. No.: WO2011/046807
PCT Pub. Date: Apr. 21, 2011

(65) Prior Publication Data
US 2012/0200694 A1 Aug. 9, 2012

Related U.S. Application Data

(60) Provisional application No. 61/250,809, filed on Oct. 12, 2009, provisional application No. 61/278,936, filed on Oct. 13, 2009.

(51) Int. Cl.
G06K 9/36 (2006.01)
G01N 21/64 (2006.01)

(52) U.S. Cl.
CPC .................. *G01N 21/6456* (2013.01)

(58) Field of Classification Search
CPC ....................................................... G06K 9/36
USPC ....................................................... 382/128
See application file for complete search history.

(56) References Cited

U.S. PATENT DOCUMENTS 4,288,323 A 9/1981 Brigante
5,162,990 A 11/1992 Odeyale et al.
(Continued)

FOREIGN PATENT DOCUMENTS

CN 101216601 A 7/2008
EP 1681015 A1 7/2006
(Continued)

OTHER PUBLICATIONS

Cellular context in epigenetics: Quantitative multicolor imaging and automated per-cell analysis of miRNAs and their putative targets James R. Mansfield. Oct. 2010.*
(Continued)

*Primary Examiner* — Stephen R Koziol
*Assistant Examiner* — Delomia L Gillard

(57) ABSTRACT

Multiple modality contrast can be used to produce images that can be combined and rendered to produce images similar to those produced with wavelength absorbing stains viewed under transmitted white light illumination. Images obtained with other complementary contrast modalities can be presented using engineered color schemes based on classical contrast methods used to reveal the same anatomical structures and histochemistry, thereby providing relevance to medical training and experience. Dark-field contrast images derived from refractive index and fluorescent DAPI counterstain images are combined to produce images similar to those obtained with conventional H&E staining for pathology interpretation. Such multi-modal image data can be streamed for live navigation of histological samples, and can be combined with molecular localizations of genetic DNA probes (FISH), sites of mRNA expression (mRNA-ISH), and immunohistochemical (IHC) probes localized on the same tissue sections, used to evaluate and map tissue sections prepared for imaging mass spectrometry.

15 Claims, 19 Drawing Sheets

(56) References Cited

U.S. PATENT DOCUMENTS

| | | | |
|---|---|---|---|
| 5,249,077 A | | 9/1993 | Laronga et al. |
| 6,007,994 A | * | 12/1999 | Ward et al. ............... 435/6.11 |
| 6,195,451 B1 | | 2/2001 | Kerschmann et al. |
| 6,259,557 B1 | | 7/2001 | Miyashita et al. |
| 6,403,947 B1 | | 6/2002 | Hoyt et al. |
| 6,649,138 B2 | | 11/2003 | Adams et al. |
| 6,682,596 B2 | | 1/2004 | Zehnder et al. |
| 6,704,140 B1 | | 3/2004 | Richardson |
| 6,815,064 B2 | | 11/2004 | Treadway et al. |
| 7,202,472 B2 | | 4/2007 | Schmucker et al. |
| 7,551,349 B2 | | 6/2009 | Vodyanoy et al. |
| 2002/0150927 A1 | | 10/2002 | Matray et al. |
| 2003/0236458 A1 | * | 12/2003 | Hochman ............... 600/431 |
| 2006/0204071 A1 | * | 9/2006 | Ortyn et al. ............ 382/133 |
| 2007/0167697 A1 | | 7/2007 | Avila et al. |
| 2008/0074644 A1 | | 3/2008 | Levenson et al. |
| 2008/0074649 A1 | | 3/2008 | Levenson et al. |
| 2008/0097198 A1 | | 4/2008 | Miwa et al. |
| 2008/0139931 A1 | | 6/2008 | Butz et al. |
| 2008/0212866 A1 | | 9/2008 | Lett et al. |
| 2008/0317325 A1 | * | 12/2008 | Ortyn et al. ............ 382/133 |
| 2009/0074264 A1 | * | 3/2009 | Pekar et al. ............ 382/128 |
| 2009/0088332 A1 | | 4/2009 | Ju et al. |
| 2009/0129650 A1 | | 5/2009 | Hawkes et al. |
| 2009/0159789 A1 | * | 6/2009 | Yamaguchi ............ 250/281 |
| 2010/0227316 A1 | | 9/2010 | Suzuki et al. |
| 2010/0232675 A1 | * | 9/2010 | Ortyn et al. ............ 382/134 |
| 2010/0246927 A1 | * | 9/2010 | Arbuckle ............ 382/133 |
| 2011/0026803 A1 | * | 2/2011 | Can et al. ............ 382/133 |
| 2011/0074944 A1 | * | 3/2011 | Can et al. ............ 348/79 |
| 2012/0029346 A1 | * | 2/2012 | Leevy et al. ............ 600/427 |
| 2012/0112098 A1 | * | 5/2012 | Hoyt ............ 250/459.1 |
| 2013/0221240 A1 | * | 8/2013 | Kishima et al. ............ 250/459.1 |

FOREIGN PATENT DOCUMENTS

| | | |
|---|---|---|
| EP | 1780672 A1 | 5/2007 |
| JP | 2008-224465 | 9/2008 |
| KR | 20070038725 A | 4/2007 |
| WO | 00/70541 A1 | 11/2000 |
| WO | 0068434 A2 | 11/2000 |
| WO | 2006084155 A1 | 8/2006 |
| WO | 2008098357 A1 | 8/2008 |
| WO | 2008116068 A1 | 9/2008 |

OTHER PUBLICATIONS

Multispectral Imaging and Pathology: Seeing and Doing More. Levenson et al. 2008.*

Chan, P. et al, "Method for multiplex cellular detection of mRNAs using quantum dot fluorescent in situ hybridization," Nucleic Acids Research, 2005, vol. 33, No. 18, 8 pages.

Flajshans, M. et al, "The application of image cytometry to viability assessment in dual fluorescence-stained fish spermatozoa," Cell Biology International 28, 2004, pp. 955-959.

Heemskerk, J. et al, "Collagen But Not Fibrinogen Surfaces Induce Bleb Formation, Exposure of Phosphatidylserine, and Procoagulant Activity of Adherent Platelets: Evidence for Regulation by Protein Tyrosine Kinase-Dependent Ca2+ Responses," Blood, 1997, 90, pp. 2615-2625.

Osunkoya, A. et al, "The Symphony protocol for H&E staining of prostatic adenocarcinoma on needle biopsy: a multicentre analysis of 120 cases," Pathology, Aug. 2008, 40(5), pp. 450-456.

McGrath, K. et al, "Multispectral Imaging of Hematopoietic Cells: Where Flow Meets Morphology," J. Immunol. Methods, Jul. 31, 2008, 336(2), pp. 91-97.

Ruthenberg, R. "Universelles Fluoreszenzmikroskop, Fluoreszenz-Phasenkontrast-Mikroskop fur zahlreiche Anwendungen," BIOspekturm Jun. 2006. 12Jahrgang, pp. 638-639.

Hall, John Charles, "On an easy method of viewing certain of the diatomaceae," Quarterly Journal of Microscopical Science, 1856, S-14, Issue 15: 205-208.

Ploem, J.S, "The Use of a Vertical Illuminator with Interchangeable Dichroic Mirrors for Fluorescence Microscopy with Incident Light," Zeitschrift fur wissenschaftliche Mikroskopie und mikroskopische Technik, 1967, vol. 68, Issue 3: pp. 129-142.

Kohler, A. "Gedanken zu einem neuen Belechtungsverfahren fur mikrophotographische Zwecke," Zeitschrift fur wissenschaftlich Mikroskopie, 1893, pp. 433-440.

Malik, Z. et al. "Fourier transform multipixel spectroscopy for quantitative cytology," Journal of Microscopy, May 1996, vol. 182, Pt 2, pp. 133-140.

Bolte, S. & Cordelieres, F.P., "A guided tour onto subcellular colocalization analysis in light microscopy," Journal of Microscopy, vol. 224, 2006, pp. 213-232.

Richard M Levenson et al: "Multispectral imaging and pathology: seeing and doing more", Expert Opinion on Medical Diagnostics, vol. 2, No. 9, Sep. 2008, pp. 1067-1081.

* cited by examiner

FIG. 8B Subtractive Overlay

FIG. 8A Additive Overlay

MULTI-MODALITY CONTRAST AND BRIGHTFIELD CONTEXT RENDERING FOR ENHANCED PATHOLOGY DETERMINATION AND MULTI-ANALYTE DETECTION IN TISSUE

CROSS REFERENCE TO RELATED APPLICATIONS

This application claims the benefit of U.S. Provisional Application No. 61,250,809 filed on Oct. 12, 2009, and U.S. Provisional Application No. 61/278,936 filed on Oct. 13, 2009, which applications are incorporated by reference herein in their entirety.

FIELD

The disclosure pertains to methods of providing contrast in tissue sections for pathology determination.

BACKGROUND

Microscopic clinical examination of conventional histological stained tissue sections can be used to evaluate tissue structures and morphological patterns of diagnostic significance. Skilled physicians can view such histological stained tissue sections for diagnosis, and to design and evaluate treatments. The contrast of structures provided by such images using classical stains is familiar, and permits the physician to devote her efforts to interpreting anatomical and morphological tissue section features and anomalies, and not on trying to translate how the staining procedure reveals features relevant to her medical training and experience.

Additional tissue imaging techniques are being developed that promise to enhance the correlative diagnostic information obtainable by the physician on valuable biopsy material and archived tissue specimens. For example, fluorescence microscopy can be used for detection of specialized molecular markers, but fluorescence based images typically lack the familiar structural and anatomical context information found in tissue stained with hematoxylin and eosin (H&E) and viewed using brightfield microscopy.

While fluorescence based images provide useful molecular information for confirming and characterizing disease states, conventional histological stained sections remain necessary for pathology determination on tissue. Typically, serial tissue sections through a specimen must be prepared and evaluated. Commonly, the serial sections include a conventional H&E stained section and specially stained section(s) for diagnostic molecular markers. Comparing serial sections not only increases the cost and time necessary for an evaluation, it may be difficult or impossible to correlate features found in one section with features found in the other. Serial sections can be lost or destroyed in the staining process pipeline as well.

SUMMARY

The technology described herein provides methods and apparatus that use multi-modal contrast to produce complimentary contrast components segmented and displayed in a manner relevant to physician training and experience for pathology analysis. Such complimentary contrast modes may be streamed to display to permit navigation of tissue structure, focusing, and changes of magnification. Tissue sections can contain one or more probes targeting particular molecules or chemistries of interest. Color contrast of tissue structure is provided that can be comparable to the contrast produced with conventional color absorbing histological stains such as hematoxylin and eosin stain (hereinafter "H&E"). The images produced by one or more of the disclosed methods can also include features revealed using additional markers and optical or chemical contrast modes. Typically, correlation of differentially labeled features between different tissue sections becomes unnecessary. The images are presented in digitally rendered color brightfield context to provide an image appearance that is comparable to that produced in conventional histological slides that have been stained to reveal the same structural features.

In some disclosed examples of multi-modal contrast, contrast is derived from the refractive index properties and fluorescent labeling of tissue specially prepared for markers of specific molecules. These examples demonstrate the complimentary combination of transmitted-light darkfield refraction contrast imaging, with simultaneous incident light fluorescence imaging of nuclear counterstain, and the interrogation of multiplexed molecular probes. Corresponding correlative images are obtained either simultaneously (in parallel) or sequentially (in serial). In some examples, illumination wavelengths and detection wavelengths used to create contrast on unstained or stained tissue may be tightly controlled to promote unambiguous segmentation and to prevent interference with multiplexed probes. Molecule-specific probe localizations for protein antigens, mRNA expression, or genetic rearrangements in DNA can be overlaid on the specimen structure. This contrast is associated with changes in refractive index due to tissue structure as preserved and resolved through the use of specific histological processing. In typical examples, disclosed methods provide image contrast based on refractive index variations in tissue moieties in combination with fluorescent counterstains to provide color pathological context for molecule-specific multiplexed probes. Examples include formalin-fixed, paraffin embedded tissues and frozen tissue. Refractive index contrast can be derived directly from the refractive or scattering properties of tissue and probe moieties, or from amplitude of a phase-shift, or a rate of change of a phase-shift gradient.

Some disclosed methods comprise exposing a fluorescently stained specimen to a stimulus beam selected to produce fluorescence by the fluorescent stain, and producing a corresponding fluorescence image. The same specimen is also exposed to a high NA circumferential dark field illumination, and a corresponding dark field image representing changes in refractive index and light scattering moieties is produced. In some examples, the fluorescence stimulus beam exposure and the dark field refraction illumination field exposure are applied simultaneously, and the complementary images are obtained in parallel. In other examples, the fluorescence image and the dark field refraction contrast image are recorded serially. Imaging apparatus according to examples comprise a multi-modal optical system configured to produce a transmitted dark-field illumination field and an incident illumination fluorescence excitation optical system. These sub-systems are configured to produce multiple complimentary images that can be combined for correlative analysis: a refractive contrast image based on properties of the prepared tissue, a fluorescence image of a nuclear counterstain, and a plurality of fluorescent images representing various molecular markers that can be segmented by emission wavelength. At least one image capture device is coupled to receive the dark field and fluorescence images and an image processor is configured to record and process the dark field image and the fluorescence images and produce a combined image.

Computer readable storage media comprise computer-executable instructions for receiving images associated with multiple modes of contrast associated with common portions of a specimen section prepared for pathological examination, and overlaying the multiple modes of contrast to produce a combined image.

In some examples, the image processor is configured to produce a pseudo-color bright field rendering of the combined image based on the recorded refraction contrast dark-field image and fluorescent images. The fluorescence image and the dark field refraction image are individually colored, combined and inverted to produce a combined color image in an apparent brightfield context with contrast relevant to conventional staining. Specific color mappings to facilitate straightforward physician interpretation are applied to the refraction contrast image, fluorescent nuclear counterstain, and specific fluorescent probes. These images are subsequently combined to produce a combined-color recorded image in brightfield rendering. In some examples, the color mapping is based on quantitative measures of human perception of preferred color for pathology determination associated with at least one color-absorbing histological stain such as an eosin stain. In still further examples, a color lookup table is applied to a fluorescence image, wherein the color mapping is associated with at least one contrasting color-absorbing histological stain such as a hematoxylin stain. In some examples, color lookup tables are applied to the dark-field refraction image and the fluorescence counterstain image so as to produce an image having inverted contrast associated with complimentary color hue, inverted value and inverted saturation compared to that encountered in ideal hematoxylin and eosin staining. In other examples, the specimen imaged optically is prepared for further imaging using mass spectrometry to provide molecular mapping.

These and other features and aspects of the disclosed technology are described below with reference to the accompanying drawings.

BRIEF DESCRIPTION OF THE DRAWINGS

FIG. 7 (1c-3c) shows the images of FIG. 7 (1a-3a) and FIG. 7(1b-3b) after being combined.

FIG. 8A is an additive overlay to a multi-mode pseudo-bright field image using QDot probes with 565 nm and 655 nm emission wavelengths from a DAPI counter-stained formalin fixed paraffin embedded specimen. FIG. 8B is a subtractive overlay in which pseudo-color probe images are subtracted from the facsimile H&E rendered image.

DETAILED DESCRIPTION

Figure 1:
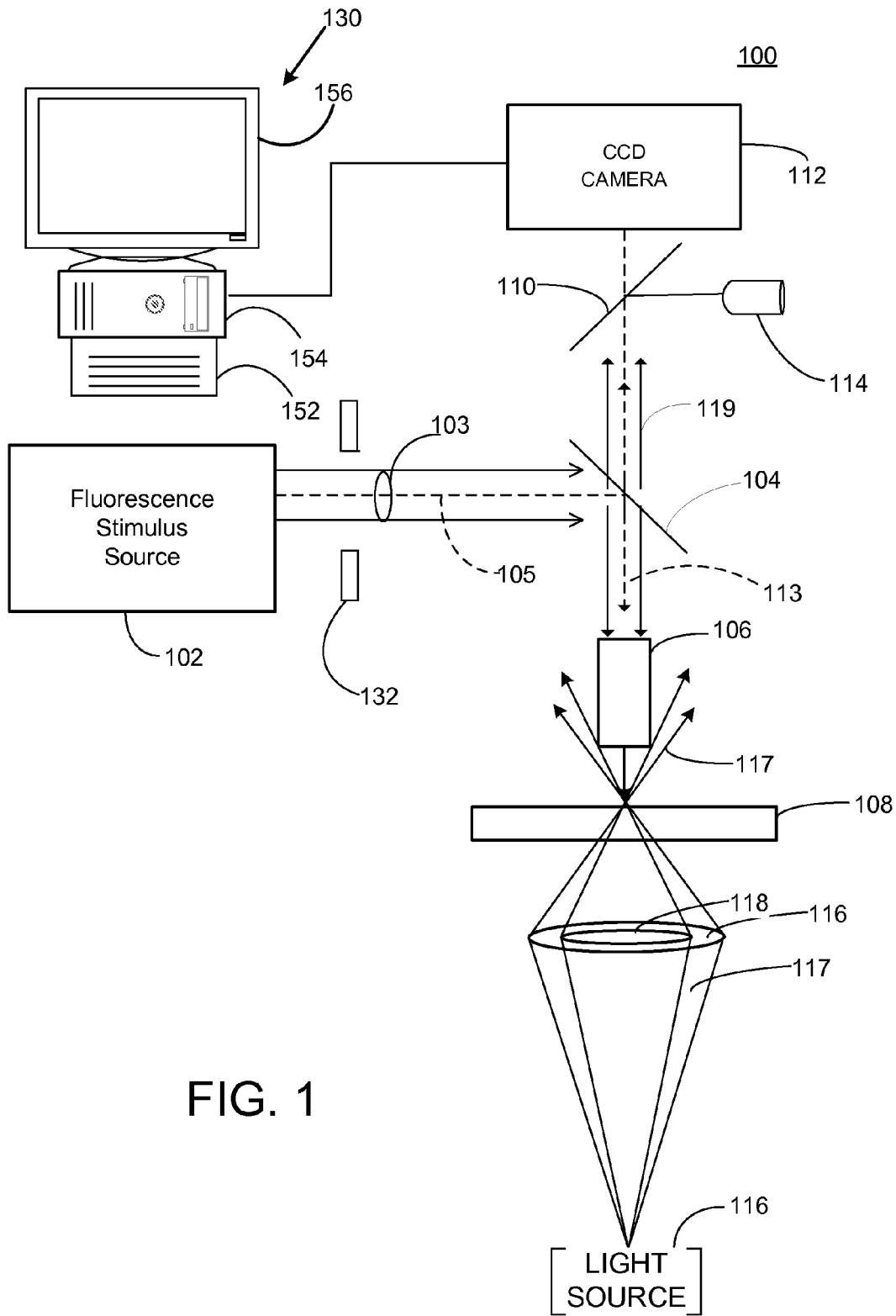
FIG. 1 is schematic diagram of a representative imaging system that provides both refraction-contrast dark field and fluorescence-based images.

As used in this application and in the claims, the singular forms "a," "an," and "the" include the plural forms unless the context clearly dictates otherwise. Additionally, the term "includes" means "comprises."

The systems, apparatus, and methods described herein should not be construed as limiting in any way. Instead, the present disclosure is directed toward all novel and non-obvious features and aspects of the various disclosed embodiments, alone and in various combinations and sub-combinations with one another. The disclosed systems, methods, and apparatus are not limited to any specific aspect or feature or combinations thereof, nor do the disclosed systems, methods, and apparatus require that any one or more specific advantages be present or problems be solved.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed systems, methods, and apparatus can be used in conjunction with other systems, methods, and apparatus. Additionally, the description sometimes uses terms like "produce" and "provide" to describe the disclosed methods. These terms are high-level abstractions of the actual operations that are performed. The actual operations that correspond to these terms will vary depending on the particular implementation and are readily discernible by one of ordinary skill in the art.

Theories of operation, scientific principles, or other theoretical descriptions presented herein in reference to the apparatus or methods of this disclosure have been provided for the purposes of better understanding and are not intended to be limiting in scope. The apparatus and methods in the appended claims are not limited to those apparatus and methods which function in the manner described by such theories of operation.

Introduction

Multiple modes of complimentary contrast generation in tissue can permit visualization of anatomical and morphological tissue context, presented in a brightfield context familiar to the trained physician, along with localizations of probes for specific molecules or variations in tissue chemistry. Multimodal contrast may leverage a plurality of light-tissue and probe detection interactions so long as the information provided is complementary. Tissue prepared for pathological examination has constitutive optical activity and the optical qualities produced by a particular protocol can be optimized to produce useful contrast qualities when combined with appropriate imaging instrumentation.

Image contrast for non-fluorescent structures can be provided through components of optical activity engineered into, or preserved in, a particular tissue preparation scheme such as used in automated staining protocols on formalin fixed paraffin embedded as well as frozen tissue. This enhanced optical activity may be digitally recorded and rendered in artificial bright field contrast to visualize and highlight structures such as the extracellular matrix, nucleoli and cell membranes. Such visualization capabilities are used to diagnose anomalous growth patterns and morphology characteristic of pathological conditions in tissue. Multiple modes of optical or activity or chemical properties in prepared tissue can be recorded, in serial or in parallel, and digitally converted into bright field image contrast for visualization, and is referred to herein as "pseudo bright field."

Representative imaged structures are of pathological significance and can be used by physicians in tissue screening and in the diagnosis of pre-cancer and cancer disease states, as well as for other diagnostic purposes, and in the evaluation of treatment effectiveness. In an unstained or specially stained tissue section, such morphological structures and anatomical context can be practically invisible under single-mode contrast methods such as conventional transmitted light brightfield or fluorescence detection. Complimentary multiple modality imaging methods can produce medically relevant structural information and present this information in a readily interpretable format without the use of conventional light absorbing stain. Quantitative values can be measured and recorded based using one or more sets of computer-executable instructions provided by one or more computer readable storage media. Morphological metrics can be leveraged to correlate such morphological characteristics to the molecular information contained in the same tissue; this approach may help in ongoing efforts to stratify disease condition and prognosis as well as monitor treatment efficacy. Digital multi-modality images of tissue sections can be captured simultaneously and rendered using distinctive colors for complimentary feature components and streamed or otherwise stored or delivered for examination by a pathologist or other clinician in near real-time. Such methods facilitate high complexity tissue-based diagnostics development and permit leveraging physician medical training and experience with conventional histological stains. Molecular data, including that from immunohistochemistry, DNA hybridization, mRNA hybridization probes, lectins, and mass spectrometry and other analyses can be integrated for individual tissue sections, and reported rapidly in a format that is familiar and pertinent to the practicing pathologist.

The examples provided herein leverage a multi-modality imaging strategy utilizing dual-illumination paths for providing images with complementary contrast of protein structure, and DNA counterstain, as well as molecule-specific markers for medical diagnosis and evaluation. The example approach includes a combination of dark-field refraction and fluorescence contrast; these complimentary contrast modes are digitally rendered using specialized color tables derived from physician preferences of classical histological stain qualities. With such a combination, multi-color contrast in tissue samples similar to that obtained in samples stained using classical histological methods such as the hematoxylin and eosin (H&E) stain can be provided. Such images can be used to develop regions of interest for further molecular analysis using luminescent, fluorescent, scattering, or absorbing probes for protein, lipid or carbohydrate antigens, mRNA or DNA, probes for charge properties or for imaging mass spectrometry (IMS). The multimodal contrast illumination contrast scheme exemplified herein can provide contextual information of tissue sections in a manner consistent with common stain/counterstain combinations used in conventional histological methods. For convenience, optical radiation beams that are directed to a specimen to obtain images are referred to herein as stimulus beams. In some examples, stimulus beams are selected to produce fluorescence in one or more portions of the specimen, and may or may not be at visible wavelengths. Other stimulus beams include illumination beams that are at visible wavelengths for direct viewing. Stimulus beams can also be based on other types of radiation as well, including in other wavelength ranges and charged particle beams or acoustic beams.

In some examples, such methods and apparatus have been applied to fluorescence in situ hybridization (FISH), immunohistochemistry (IHC), and mRNA in situ hybridization (mRNA-ISH) applications in formalin-fixed paraffin-embedded tissues. Quantum dot (QDot)-labeled FISH probes, QDot labeled IHC probes and QDot labeled mRNA-ISH probes were specifically detected on tissue using multi-modal contrast and digital pseudo-brightfield rendering for visualization of probe localizations within the tissue anatomical structure context. In typical examples, a dark field refraction contrast image, a counter-stained image obtained with a fluorescent nuclear stain, and one or more probes imaged using fluorescent QDot detection are combined. These and other examples are described below.

Representative Imaging Systems

A representative example of a suitable imaging system 100 is illustrated in FIG. 1. A fluorescence stimulus light source 102 is situated to deliver a stimulus beam 103 along an axis 105 to a wavelength dependent beamsplitter (dichroic) 104. The light source 102 is typically a light emitting diode (LED), metal halide or other arc lamp, but other incoherent or coherent light sources such as lasers can be used. As shown in FIG. 1, the dichroic 104 reflects the stimulus beam 103 to an objective lens 106 which in turn directs the stimulus beam 103 to a specimen 108. In typical examples, the specimen 108 is selectively labeled with one or more fluorophores that produce fluorescence in response to the stimulus beam 103. A portion of the fluorescence is collected by the objective lens 106 and directed along an axis 113 through the dichroic 104 to an optional beam splitter 110. The beam splitter 110 directs a portion of the fluorescence to a camera 112 so that a specimen image can be recorded, viewed, or analyzed at a computer system 130. Another portion of the fluorescence is directed to an eyepiece 114 for direct viewing of the specimen 108 based on the fluorescence light. In addition, a shutter 132 or other beam modulator can be provided to substantially prevent the stimulus beam 103 from reaching the specimen 108, or the fluorescence source can be controlled (via the computer system 130 or manually) so that no stimulus beam is produced. Wavelengths of light used for the stimulus beam can be selected as convenient. Typically the stimulus beam includes primarily optical radiation at wavelengths or in a wavelength range that is suitable for generating fluorescence light in fluorescent dyes or fluorophores associated with any selective markers applied to the specimen. Typical wavelength ranges for the stimulus beam is between about 300-550 nm, but shorter or longer wavelengths can be used.

In addition to the fluorescence imaging system, a refractive contrast imaging system using circumferential oblique dark field illumination is provided. In the example of FIG. 1, the circumferential oblique field illumination 117 is selected so that in the absence of refractive index differences or scattering moieties in the specimen, light flux does not reach the CCD camera 112 or the eyepiece 114, and only refractive index transitions appear. By using different magnification objective lenses with the same numerical aperture (acceptance angle) or by using a secondary magnification lens, the same illumination optimizations for refraction imaging can be used at multiple optical magnifications. There are multiple strategies to create contrast based on refraction or scattering of the illumination field. Such refractive index contrast images are referred to herein as "dark field" images. A substage condenser system 116 is situated so as to deliver an oblique field illumination 117 to the specimen 108 at substantially the same location as that illuminated by the stimulus beam 103. The substage condenser system 116 can direct a suitable light source such as an LED, tungsten halogen lamp, an arc lamp, or other light source and one or more lenses, mirrors, filters, polarizing elements, phase plates, prisms, annuli or apertures that can produce a suitable beam. In the example of FIG. 1, the oblique field illumination 117 is produced by a carefully sized annulus, but in other examples, different approaches to field illumination or point scanning, line scanning, edge illumination, or other strategies designed to produce refraction contrast can be provided. In the example of FIG. 1, so-called "dark field" illumination is provided in which only portions of the field illumination that are scattered or redirected by the specimen 108 are collected by the numerical aperture of the objective lens 106 and reach the camera 112 or the eyepiece 114. The camera 112 and the eyepiece 114 are situated so as to form an image of the specimen 108 based on the redirected portions of the transmitted light. Typically, the transmitted illumination system 117 can be shuttered or its light source deactivated as desired so that fluorescence-based images can be acquired or viewed independently of the transmitted illumination. The example microscope system 130 of FIG. 1 thus permits recordation of specimen images and viewing of a specimen based on fluorescence, dark field refraction contrast, or both, either simultaneously or sequentially.

Using transmitted circumferential oblique illumination such as illustrated in FIG. 1, contrast can be produced based on interfaces and transitions between specimen portions having different refractive indices. Typically, the condenser system 116 includes an annulus 118 of an appropriate size (and can be added to a conventional condenser) in the transmitted light path of a compound microscope equipped with a transmitted light source. In this way, structures that refract and scatter light have appreciable contrast in images without the use of a light absorbing color stain. The transmitted illumination wavelength can be spectrally filtered with, for example, a near IR filter or other filters or combinations of filters so that spectral images of fluorescent probes can be obtained with transmitted contrast collected at a longer wavelength in the same data acquisition with both illumination sources active simultaneously. The refraction field illumination is generally selected to provide a suitable visual image for recording, and is in a wavelength range of between about 400 nm and 900 nm, but different spectral regions within this range can be used if desired. In other examples, reflected dark field illumination is used in which the oblique illumination and the objective lens are situated on the same side of the specimen.

The specimen dark field image can be obtained by itself through segmenting fluorescence with one or more filters, shuttering or temporally modulating or otherwise blocking the stimulus beam. In some examples, the fluorescence-based image can be obtained with a suitable filter tuned to the fluorescence wavelength and the refraction contrast filtered to a different wavelength range; these different wavelength ranges can be separated to different sensors, directed to different portions of the same sensor or recorded sequentially. The unwanted contribution of dark field illumination to the fluorescence image or images, or vice versa, can be reduced by spectrally filtering, but shuttering either the dark field illumination field or the fluorescence light path is possible. In addition, the dark field and fluorescence images can be viewed separately or simultaneously.

The camera 112 is typically a monochrome charge coupled device (CCD) or complementary metal oxide semiconductor (CMOS) camera though other image sensors such as electron multiplying CCD (EMCCD) and intensified CCD (ICCD) sensors may be used. Wavelength filters, dispersive elements, phase plates, prisms, polarizing elements, tunable optical crystals and other optical and electro-optical methods can be used to modify the optical radiation reaching the CCD and/or the eyepiece so as to produce one or more corresponding monochromatic images in the selected wavelength ranges. In some cases, fluorescence reaching the camera 112 can be spectrally resolved in a plurality of wavelength bins, and a corresponding plurality of fluorescence images obtained for analysis. Spectral analysis can be performed with a plurality of absorptive or reflective filters, a prism, or a diffraction grating that are inserted into the path of the fluorescence. Generally, spectral resolution can be achieved using interferometric, dispersive, or absorptive optical systems under the control of the computer system 130 or inserted manually. While images can be recorded as one, two, or three dimensional arrays of picture elements with values associated with a received light flux intensity (either from fluorescence or other modes of contrasting illumination), images can be recorded in other formats and complex data structures if desired. For convenience in this description, an image refers to a 2-D mapping of data in a structured array as viewed by a clinician through a microscope or other viewing apparatus and a recorded image refers to data values stored, processed and/or displayed based on an image received by a CCD or other image sensor.

As noted above, a plurality of spectral images can be obtained based on fluorescence and transmitted illumination or both. Spectroscopic information at each pixel of an image can be gathered and the resulting data analyzed with spectral image-processing software. A series of images can be derived that represent intensities at different wavelengths that are electronically and continuously selectable and then evaluated with an analysis program designed for handling such data. In some examples, quantitative information from multiple fluorescent signals and/or optical contrast modalities can be evaluated simultaneously.

The image sensor 112 is coupled to the computer system 130 that includes a keyboard, 152, a processing unit 154, and a display 156. In some examples, one or more additional user input devices such as joysticks, mice, or digitizing tablets, and one or more additional output devices such as printers or displays are provided. The processing unit 154 typically includes a microprocessor and one or more computer readable storage media such as read only memory (ROM), random access memory (RAM), a hard disk, a floppy disk, a compact disk or digital video disc for storage of image data and computer executable instructions for recordation, transmission, analysis, and processing of images or image data.

In typical examples, the computer system 100 is coupled to one or more other computer systems via a wired or wireless network connection, and in some examples, is coupled to the Internet. Although image processing operations can be conducted at a single computer system, in some examples, image data or images are processed at a plurality of computing systems that can be situated in a common location or distributed on a network. While laptop computers can be convenient, other computing devices such as desk top computers, workstations, handheld computers, netbook computers, or other devices can be used for image capture and processing. In some examples, image data can be processed and specimen evaluations can be provided without a display, and evaluations communicated via the network connection (by email for example), sent to a printer, or delivered as a text or multimedia message using a cell phone network.

The imaging system 100 is one example of a suitable imaging system. In other examples, a reflective or catadioptric objective can be used instead of the objective lens 106, a short pass filter can be used instead of the long pass filter 104 by rearrangement of the fluorescence stimulus source 102 and the camera 112 and eyepiece 114. In some examples, only a camera or an eyepiece is provided for either image recordation or image viewing. Additional mirrors or prisms can be used to fold the optical axes as may be convenient. Different strategies for multimodal contrast using phase masks, phase contrast, Rotterman contrast, oblique illumination contrast, Rheinberg contrast, interference contrast schemes, adaptive optics, laser scanning, time or frequency domain lifetime imaging, structured illumination, photoswitchable probes, polarization and anisotropy, $2^{nd}$ harmonic imaging, two-photon excitation and other strategies may be employed. Specimen positioning hardware is not shown for convenient illustration, and in many examples, binocular viewing with dual eyepieces can be provided, and suitable filters and beamsplitters can be provided so that different image outputs receive an image light flux associated with only one of multiple contrast modalities, polarization states or wavelength bandwidths. Additional filters (reflective or absorptive) can be provided, typically to reduce the magnitude of any stimulus light that reaches the camera 112 or the eyepiece 114, or to control relative light intensity or spectral content for viewing or recording.

Figure 11:
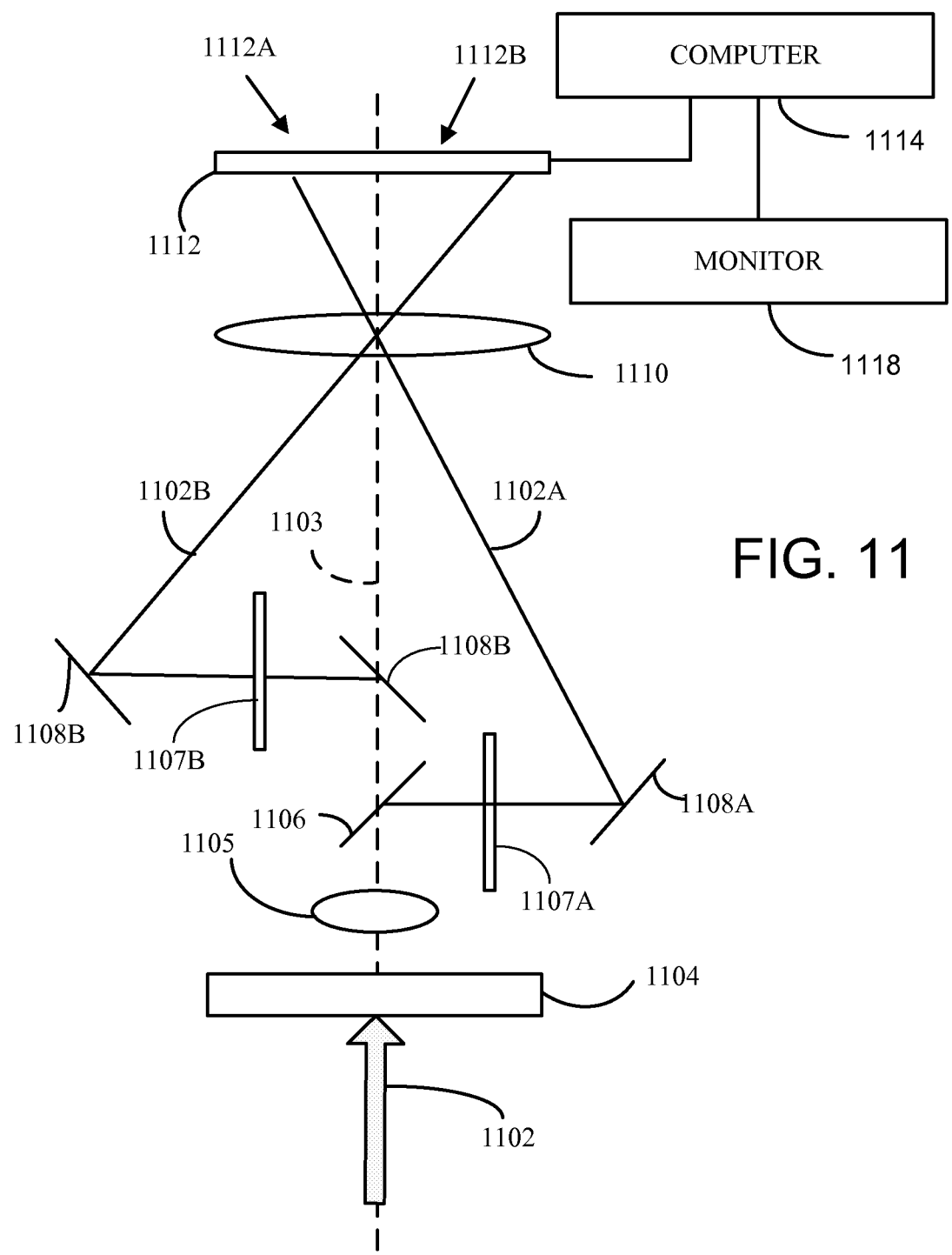
FIG. 11 is a schematic diagram of an optical system that simultaneously produces side-by-side refraction dark field images and fluorescence-based images using a single CCD camera.

Another representative imaging system is illustrated in FIG. 11. As shown in FIG. 11, a combined image light flux 1102 that includes a refraction modulated flux 1102A and a DAPI fluorescence modulated flux 1102B corresponding to dark field and DAPI images is directed along an axis 1103 through an aperture 1104 to a collimating lens 1105. The collimated, combined light flux is incident to a dichroic mirror 1106 that reflects a portion of the modulated light flux (the DAPI modulated flux 1102A in the example of FIG. 11) to mirrors 1108A and to a filter 1107A that preferentially transmits DAPI fluorescence. A lens 1110 receives the DAPI modulated flux and forms a specimen image on a first portion 1112A of a CCD or other image sensor 1112. The dichroic mirror 1106 transmits the longer wavelength refraction modulated beam 1102B to a filter 1107B selected to reject DAPI fluorescence and the associated DAPI stimulus beam. A mirror 1108B directs the modulated flux 1102B to the lens 1110 which forms a dark field image on a portion 1112B of the CCD 1112. The CCD 1112 is coupled to a computer or other processing device that can store image data from the CCD 1112 in memory, and provide image data to a monitor 1118 or other display. With such an imaging system, dark field and fluorescence images can be obtained simultaneously and displayed side-by-side as a raw image or rapidly split into two images, color mapped and overlaid in near real-time on the monitor 1118. The configuration of FIG. 11 is illustrative only, and specimen modulated refraction and fluorescence light fluxes can be separated and used in image formation in other arrangements and using more, fewer, and different components. The images can be side by side on the CCD 1112 or processed by the computer 1114 so that a combined 2-color overlay in brightfield-rendered context can be displayed on the monitor 1118. As shown in FIG. 11, multiple fluxes (dark field and DAPI) are diverted from an initial optical axis, but in other examples, one flux can be transmitted along the initial axis and the CCD 1112 situated accordingly. The dark field and DAPI images can be produced with different lenses that can be arranged to produce a common magnification or different magnifications. Additional filters, light sources, and other components can be provided so that molecular detection label and other tissue contrast image light fluxes are provided to and imaged in one or more CCDs or portions of a single CCD 1112A, 1112B.

Color Lookup Tables and Image Inversion

Figure 2:
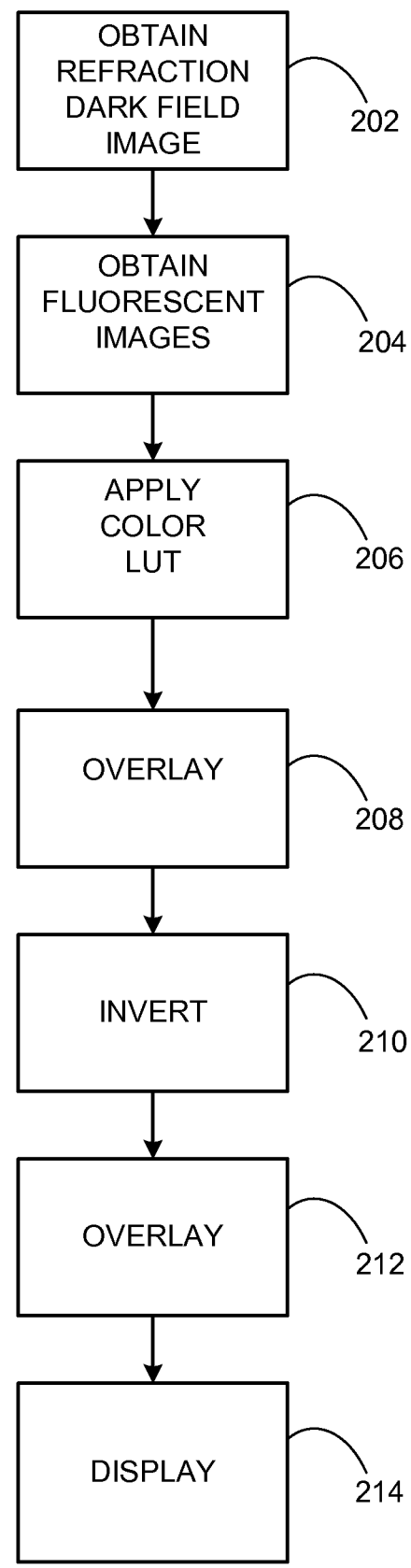
FIG. 2 is a schematic block diagram of a method of processing and combining recorded dark field and fluorescent stain based images.

The system of FIG. 1 permits multi-modality viewing and acquisition of images based on either fluorescence or dark field illumination, or both simultaneously. The acquired images can be manipulated to present specimen features in a common context using a representative method illustrated in FIG. 2. In a step 202, a dark field refraction image is recorded, typically as a monochromatic image, and in a step 204, one or more fluorescence-based images are recorded. The number of such fluorescence-based images can depend on numbers and types of fluorescent markers or dyes that are applied to the specimen. These images can use different wavelength bands corresponding to emission wavelengths of the fluorescent markers. In some examples, the different wavelength bands can be overlapping, non-overlapping, or a combination thereof.

In the step 204, the one or more fluorescence based images can be obtained corresponding to fluorescence from corresponding fluorophores. Appropriate spectral segmentation of the fluorescence light can be used to obtain multiple fluorescence based images that can reveal different specimen features, typically dependent on the specific probe associated with the fluorescent detection marker.

Upon acquisition of the images (either as each is acquired or after all or some have been acquired), one or more color map lookup tables (LUTs) can be applied to the intensity values of monochrome images in a step 206 to produce pseudo-color rendered images and these rendered images can be overlaid in a step 208. One or more or all of the hue, intensity or saturation of the acquired overlaid image is inverted in a step 210 to produce an image having the appearance of colored structure on a bright field. In a typical application of a pseudo-color LUT, pixels of monochrome images are assigned RGB color intensity values based on grey-scale pixel intensity values and vice versa. Such inversions may also invert color coordinates to produce complimentary color mappings. Image inversion generally maps large pixel intensity values to smaller pixel intensity values. For example, in an image in which pixel intensities are represented with 8 intensity values (3-bit depth), intensity values can be re-mapped as shown in Table 1.

TABLE 1

Image Inversion with 3 Bit Values

| Original | Re-Mapped |
|---|---|
| 0 | 7 |
| 1 | 6 |
| 2 | 5 |
| 3 | 4 |
| 4 | 3 |
| 5 | 2 |
| 6 | 1 |
| 7 | 0 |

Such a mapping scheme can be extended to other bit depths (e.g. 8-bit, 10-bit, 12-bit, 16-bit and others) and can be applied to different components (e.g. hue, saturation, value) of a given color space.

In the step 210, image values that would appear dark are inverted so as to appear light, and image values that would appear light are inverted so as to appear dark. The step 210 can be referred to as producing a pseudo bright field image.

The order of image inversions and pseudo-color LUTs can be varied as needed. Specific color LUTs can be selected so that, for example, a dark field image appears in color contrast similar to histological stains. In this strategy, the image modes are carefully chosen to reveal the same structures to an image produced with a conventional stain procedure such as conventional H&E staining. Images can be overlaid in a step 208 with or without color mapping for contrast components or inversion to bright field appearance. Additional color mapped images contrasting different structures can be applied to the combined image (typically overlaid with the combined image) in a step 212. The combined and processed image can be stored and/or displayed in a step 214. One or more of these steps can be omitted, duplicated, or performed in another order if more convenient.

In many practical examples, it can be advantageous to simulate the coloring of specific tissue structures produced with conventional histological stains in multimode contrast images. Such simulation provides a familiar analytical and diagnostic setting for a physician while still permitting correlation with additional specific markers to reveal additional information. This simulation also permits the elimination of light absorbing stains, so that staining does not interfere with application of other markers or the evaluation of image features revealed by these markers. For example, refraction contrast can be used to reveal extracellular and membrane proteins while a nucleus specific fluorescent dye such as DAPI can be used to reveal details of nuclear chromatin distribution. Thus, the refraction/DAPI combination can be used, with appropriate image processing, to reveal specimen features in a manner analogous to that achieved with eosin (eosinophilic, or protein-specific) and hematoxylin (nucleic acid or DNA-specific). Because these images are obtained on the same specimen, the features of each can be registered spatially and included in a displayed image for convenient analysis. Optimized color mappings can be utilized that permit images displayed as preferred by clinicians to best reveal features of interest in the context of medical training and experience. Such color mappings can be conveniently described with reference to a CIE 1976 L*a*b* color space, other color spaces such as a Hunter 1948 L,a,b color space, an CIE 1931 XYZ color space, CIE 1976 L*u*v*, HSV, HSI, HSV, HSB color, or RGB color or CMYK color values, or PANTONE or MUNSELL color scales can also be used.

Figure 3:
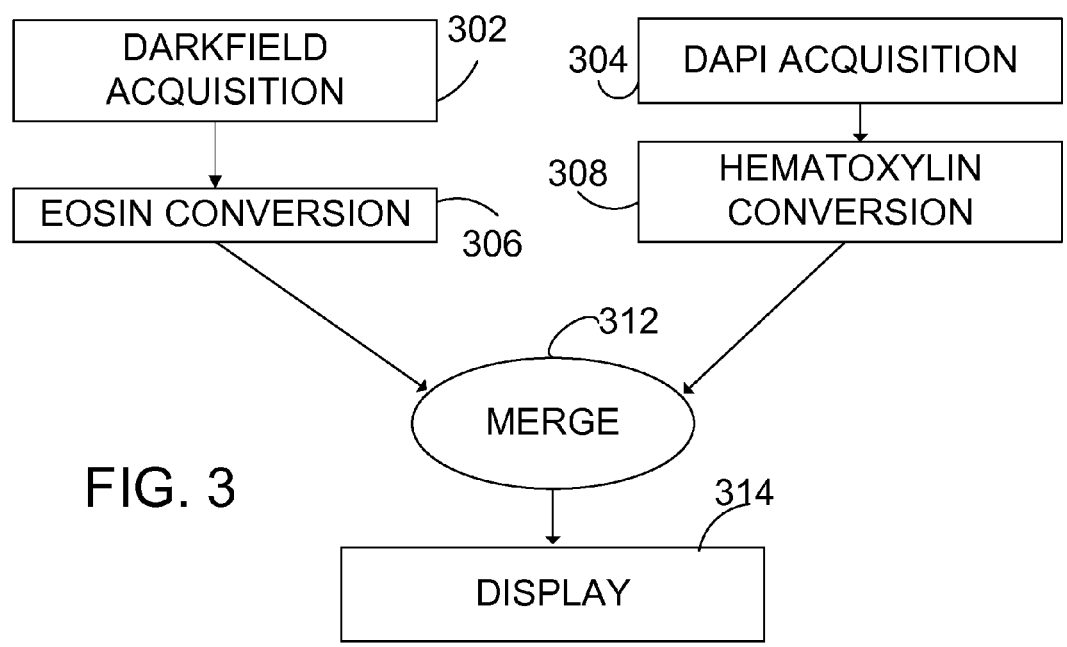
FIG. 3 is a schematic block diagram of a representative method for producing a specimen image from multiple modes of contrast with contrast corresponding to that used in pathology determination with hematoxylin and eosin (H&E) staining.

FIG. 3 illustrates a representative method 300 of specimen imaging that permits interrogation of specimen features based on refractive index contrast and DAPI fluorescence. In a step 302, a gray scale intensity map image of refraction contrast in specimen is recorded, typically using a monochrome CCD camera. In a step 304, a DAPI-fluorescence-based gray scale intensity map image of the specimen is recorded. While color filters are used in acquiring both of these images, the images are recorded as intensity values for an array of pixels as gray scale images on a monochrome CCD. In a step 306, the refractive index contrast image is processed and mapped to color to have an appearance similar to that produced with eosin color absorption under white light transmitted illumination. Eosin staining typically produces image contrast in protein moieties in the extracellular matrix and in membranes. In some examples, the step 306 can be configured so that the processed image has an appearance that is based on clinician subjective preferences for eosin staining as quantified and translated to CIE L*a*b* color space. These preferred color maps can be based either on a group of clinicians or an individual clinician. For convenience, the image resulting from the step 306 is referred to as a converted image. For processing based on eosin stains, such images can be referred to as eosin-converted images. Such converted images can be either displayed images, recorded images, or both.

In a step 308, the DAPI recorded image is processed to produce an image associated with an appearance resembling hematoxylin absorption under white light transmitted illumination. As noted above, this image can be produced based on individual or group subjective preferences, or matched using quantitative spectral color measurement and mapping to digital color space. The resulting image of the step 308 can be referred to as a converted image as well, or a hematoxylin-converted image.

The converted images are typically produced using one or more color maps or specialized lookup tables (LUTs). The images are generally pseudo-colored and inverted so that the converted image is a complimentary color, image with inverted saturation, hue and/or value. A combined image is produced by merging the complimentary images in a step 312, for example by addition, and displayed or otherwise analyzed in a step 314.

Figure 10:
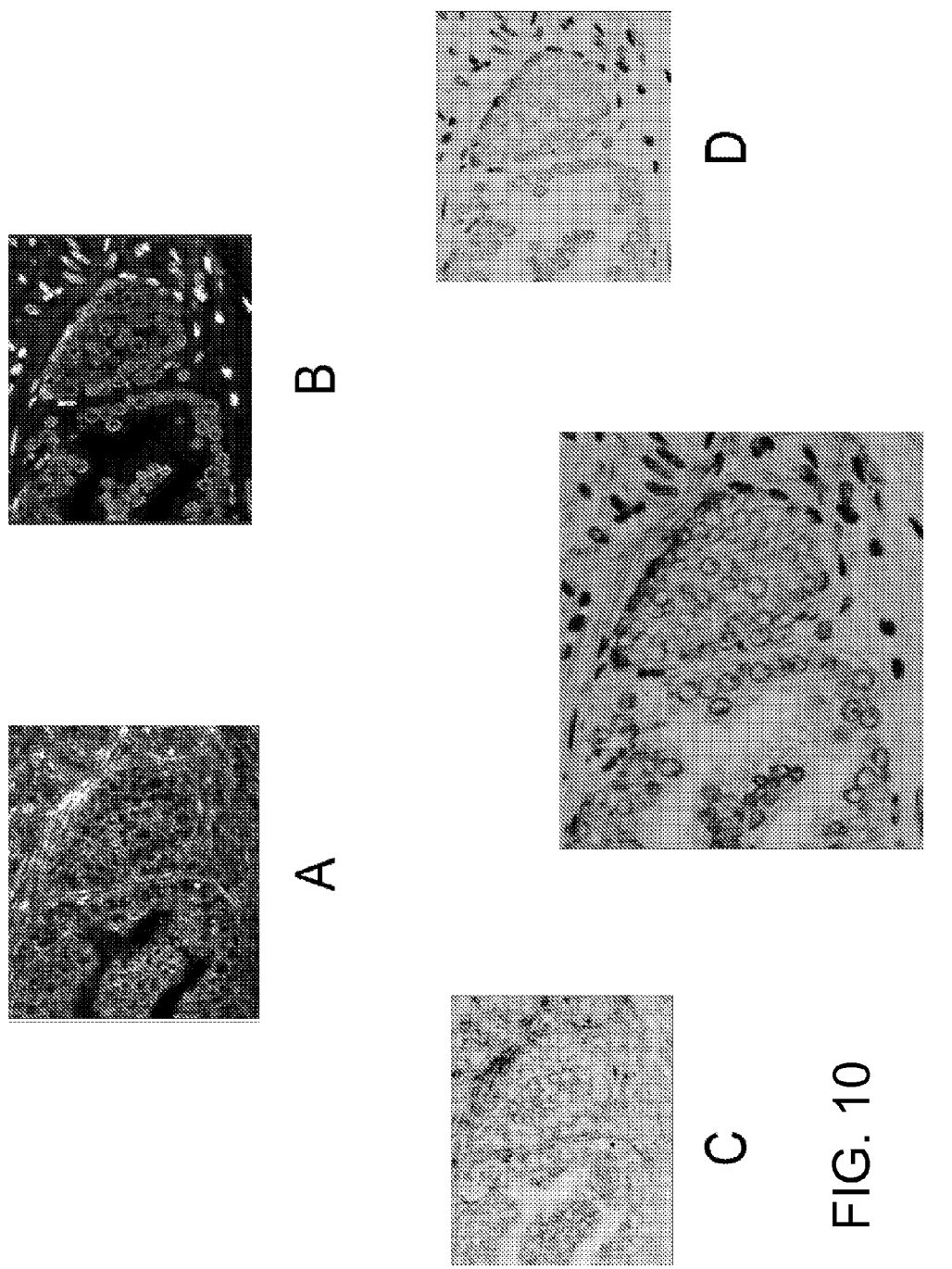
FIGS. 10A-10B are grayscale refractive index contrast and DAPI fluorescence contrast images, respectively.
FIGS. 10C-10D are CIEL*a*b* pseudo-color eosin-converted and hematoxylin-converted images based on the images of FIGS. 10A-10B, respectively.
FIG. 10E is a merged imaged obtained by combining the converted images of FIGS. 10C-10D.

The method of FIG. 3 is illustrated with human prostate specimen images shown in FIGS. 10A-10E. FIGS. 10A-10B are grayscale refractive contrast and DAPI fluorescence contrast images, respectively. FIGS. 10C-10D are eosin-converted and hematoxylin-converted images based on the images of FIGS. 10A-10B, respectively. FIG. 10E is a merged image obtained by combining the converted images of FIGS. 10C-10D. The eosin-converted image of FIG. 10C and the hematoxylin converted image of FIG. 10D are produced by application of a color LUT and image inversion.

Figure 9:
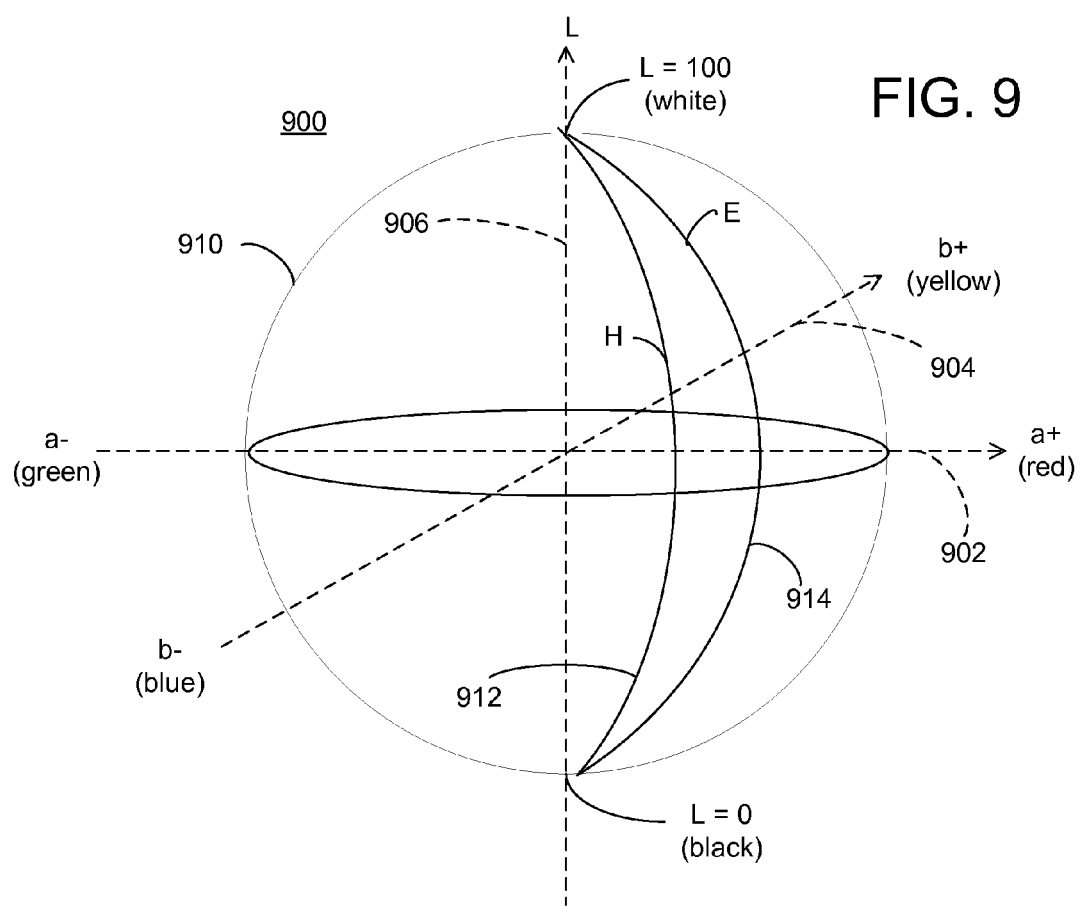
FIG. 9 illustrates an example of the CIEL*a*b* color space used to map preferential color characteristics for H&E to refraction contrast and DAPI fluorescence to render in brightfield for pathology determination.

Physician-preferential color spaces for hematoxylin and eosin stained tissues have been obtained to more closely match the pseudo-color mapping of the refractive image and DAPI counterstain to produce a preferred image appearance. Such a color mapping is illustrated in FIG. 9. Referring to FIG. 9, a CIE L*a*b* color space 900 includes an a*-axis 902, a b*-axis 904, and an L*-axis 906. CIE L*a*b* coordinates are represented as locations on a color sphere 910. Typically, color arcs 912, 914 are assigned to refractive index contrast (eosin-analogue) and DAPI fluorescence contrast (hematoxylin-analogue), respectively. It is convenient to select the color arcs 912, 914 to produce contrast similar to absorption of white light by hematoxylin and eosin in tissue, respectively. Color mapping can be provided by assigning a*,b* coordinates based on measured intensities (L*-values). The color arc 912 corresponds to a longitudinal arc on the color sphere 910 that is at an angle of about 30 degrees from the -b-axis. The color arc 914 corresponds to a longitudinal arc on the color sphere 910 that is at an angle of about 60 degrees from the -b-axis. Other arcs can be used as well. Representative coordinate ranges that produce H&E stain-like contrast for selected tissue types are summarized in Table 2 below.

TABLE 2

CIE L*a*b* Preferred Coordinate Ranges for Selected Tissues

| | CIE Lab* Ranges | | | |
| --- | --- | --- | --- | --- |
| | Cytoplasmic Features | | Nucleus Features | |
| Tissue | a* range | b* range | a* range | b* range |
| Colon | +12 to +24 | −5 to +5 | +15 to +30 | −4 to −16 |
| Liver | +30 to +50 | −4 to −16 | +38 to +52 | −15 to −27 |

Computing Environment

Figure 16:
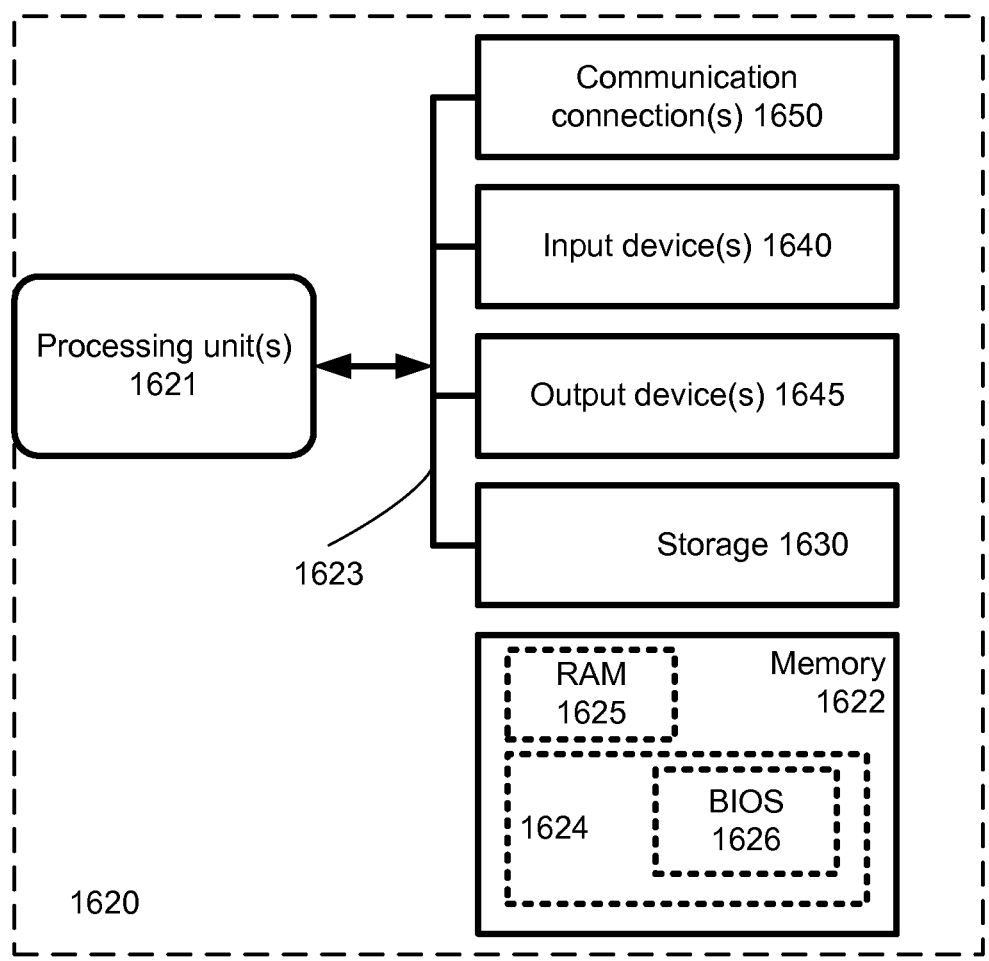
FIG. 16 is a schematic diagram illustrating a computing environment for the apparatus and methods described herein.
Figure 17:
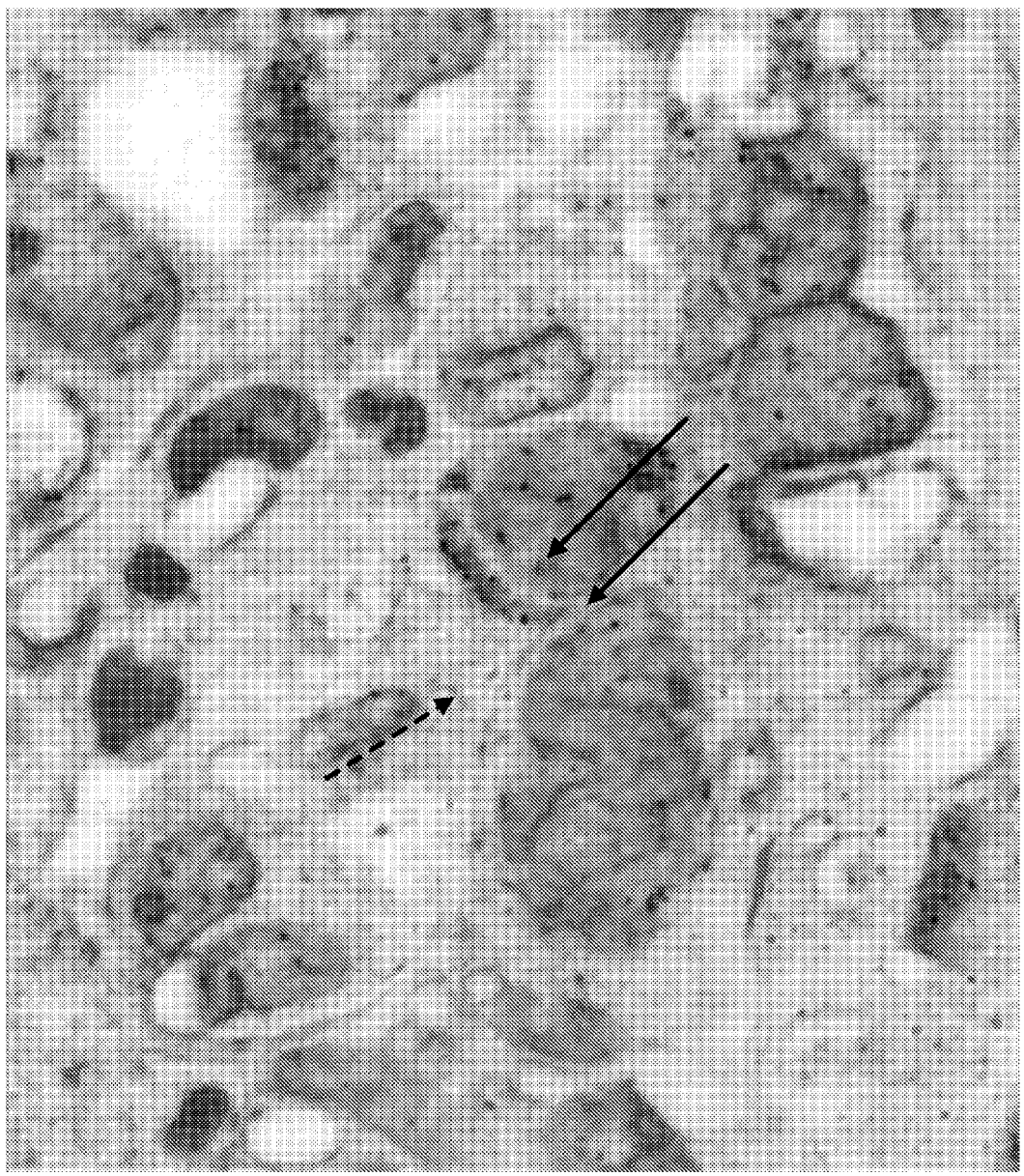
FIG. 17 is a multiple mode image providing cellular and nuclear context in brightfield rendering for a Calu-3 xenograft probed for mRNA in situ hybridization of two probes, one for ribosomal RNA (cyan color, dashed black arrow), the other for HER2 mRNA expression (black color, solid black arrows).

FIG. 16 and the following discussion provide a brief, general description of a suitable computing environment for the software (e.g., computer programs) configured to perform the methods described herein. These methods can be implemented in computer-executable instructions organized in program modules. The program modules include the routines, programs, objects, components, and data structures that perform the tasks and implement the data types for implementing the techniques described above.

While FIG. 16 shows a typical configuration of a desktop computer, the invention may be implemented in other computer system configurations, including multiprocessor systems, microprocessor-based or programmable consumer electronics, minicomputers, mainframe computers, and the like. The invention may also be used in distributed computing environments where tasks are performed in parallel by processing devices to enhance performance. For example, tasks related to measuring characteristics of candidate anomalies can be performed simultaneously on multiple computers, multiple processors in a single computer, or both. In a distributed computing environment, program modules may be located in both local and remote memory storage devices.

The computer system shown in FIG. 16 is suitable for implementing the technologies described herein and includes a computer 1620, with a processing unit 1621, a system memory 1622, and a system bus 1623 that interconnects various system components, including the system memory 1622 to the processing unit 1621. The system bus may comprise any of several types of bus structures including a memory bus or memory controller, a peripheral bus, and a local bus using a bus architecture. The system memory includes read only memory (ROM) 1624 and random access memory (RAM) 1625. A nonvolatile system 1626 (e.g., BIOS) can be stored in ROM 1624 and contains the basic routines for transferring information between elements within the personal computer 1620, such as during start-up. The personal computer 1620 can further include one or more other computer readable storage devices 1630 such as a hard disk drive, a removable memory (thumb-drive), a magnetic disk drive, e.g., to read from or write to a removable disk, and an optical disk drive, e.g., for reading a CD-ROM disk or to read from or write to other optical media. The hard disk drive, magnetic disk drive, and optical disk drive can be connected to the system bus 1623 by a hard disk drive interface, a magnetic disk drive interface, and an optical drive interface, respectively, or connected in some other fashion. The drives and their associated computer-readable media provide nonvolatile storage of data, data structures, computer-executable instructions (including program code such as dynamic link libraries and executable files), and the like for the personal computer 1620. Although the description of computer-readable media above refers to a hard disk, a removable magnetic disk, and a CD, it can also include other types of media that are readable by a computer, such as magnetic cassettes, flash memory cards, digital video disks, and the like.

A number of program modules may be stored in the drives and RAM 1625, including an operating system, one or more application programs, other program modules and program data. A user may enter commands and information into the personal computer 1620 through one or more input devices 1640 such as a keyboard or a pointing device, such as a mouse. Other input devices may include a microphone, joystick, game pad, satellite dish, scanner, or the like. These and other input devices are often connected to the processing unit 1621 through a serial port interface that is coupled to the system bus, but may be connected by other interfaces, such as a parallel port, game port, Ethernet, IEEE 1394, Gigabit Ethernet, Camera Link or a universal serial bus (USB). One or more output devices 1645 such as a monitor or other type of display device is also connected to the system bus 1623 via an interface, such as a display controller or video adapter. In addition to the monitor, personal computers typically include other peripheral output devices (not shown), such as speakers and printers.

One or more communication connections 1650 are typically provided such as wireless connections, wired connections (for example, Ethernet connections) so that that the personal computer 1620 can communicate via a communications network. In addition, although the personal computer 1620 includes a variety of input devices, output devices, memory and storage, in some examples some of these components are located remotely for access via a network. For example, processed image data obtained as discussed above can be forwarded via such a network to a remote terminal or processing system for display, evaluation, and further processing by a clinician. Data storage can be remote as well. The personal computer 1620 can be configured to record data in memory, process data according to the methods disclosed herein and display the processed data on a local monitor. However, these functions can be performed by different processing units at different locations as may be convenient.

The above computer system is provided merely as an example. The technologies can be implemented in a wide variety of other configurations. Further, a wide variety of approaches for collecting and analyzing data related to processing image data is possible. For example, the data can be collected, characteristics measured, colored, and processed to provide brightfield-context images for storage and display on different computer systems as appropriate. In addition, various software aspects can be implemented in hardware, and vice versa.

Tissue Analysis and Tissue Processing Optimization

Histological protocol is intended to preserve tissue structure and enhance contrast between structures of interest for microscopic examination. In order to accomplish this, many approaches are in use and have been used historically. Tissue fixation can involve a variety of chemistries, examples include but are not limited to such as formalin, Bouin's fixative, ethanol, glutaraldehyde, cryopreservation, microwaves, heat, acetone, the use of acids, alkaline solutions, detergents, heavy metals and many other cross-linking agents or preservatives. These different chemistries have been used to bring out details, preserve cell and tissue structures, assist in labeling and antigen retrieval and other such efforts to enhance contrast in single mode imaging for pathology. The material used to infiltrate and embed tissue and provide support to structures for microtomy and ultramicrotomy also contributes to optical characteristics. The subsequent processing, staining and mounting strategies all contribute to optical and chemical characteristics for multimodal imaging. With this in mind, studies are underway to optimize multi-modality imaging parameters and select appropriate imaging modalities specific to particular fixation, embedding, labeling and mounting conditions commonly used for histopathology. This can be done using archived tissue prepared through different conventional means and adjusting imaging parameters to enhance image quality.

The inverse approach of optimizing tissue preparation protocol to imaging modalities is also being pursued. Image quality is a synergy between tissue preparation, labeling agents, and imaging instrumentation; multi-modal imaging strategy takes this into account. Thus the tissue as well as methods of preservation and preparation are considered to be parts of the optical or chemical imaging system. Many critical physical and chemical steps are involved in tissue processing for histopathology. The principle phases of automated tissue processing represent many parameters in the processing pipeline that impact image quality. In order to best leverage particular imaging modalities that produce complimentary information, the optical and chemical qualities of tissue processing, labeling and mounting must be carefully controlled. The use of automated equipment and optimized protocols for specialized staining and consistency of reagents and chemistries are used to permit significant advances in the quality of contrast and structural/chemical resolution between complimentary imaging modalities. In the context of the examples outlined herein, the methods of tissue preparation such as protein cross-linking by formalin fixation, embedding in paraffin, deparaffin steps, preservation of nuclear chromatin, counterstaining, specific molecular probes, mounting agent and glass used for tissue preparation are all taken to contribute to the multiple modes of imaging. The multiple modes of imaging used in examples involve refractive contrast qualities and fluorescent signal and/or molecular mass resolution.

Representative Probes

Pseudo-color brightfield-rendered images based on multi-modality contrast can be combined with additional detection schemes that use various signal generation methods. Some representative probes have been described, but the disclosed technology is not limited to these examples. Some probes that are configured to specifically bind to one or more targets of interest can be coupled to a label that can be interrogated based on numerous optical and chemical-physical properties such as light absorption, emission, fluorescence lifetime, chemiluminescence, electronic characteristics, chemical characteristics, photoswitchability, intermittent blinking, radioactivity, birefringence or label mass.

Conjugates comprising signal generating moieties, such as conjugates of specific-binding moieties and signal-generating moieties, can be used for detecting specific target molecules in biological samples. The signal-generating portion is utilized to provide a detectable signal that indicates the presence/and or location of the target. Examples of signal-generating moieties include, by way of example and without limitation: enzymes, such as horseradish peroxidase, alkaline phosphatase, acid phosphatase, glucose oxidase, β-galactosidase, β-glucuronidase or β-lactamase.

When the signal-generating moiety includes an enzyme, a chromagenic compound, fluorogenic compound, or luminogenic compound can be used to generate a detectable signal. Particular examples of chromogenic compounds include diaminobenzidine (DAB), 4-nitrophenylphospate (pNPP), fast red, bromochloroindolyl phosphate (BCIP), nitro blue tetrazolium (NBT), BCIP/NBT, fast red, AP Orange, AP blue, tetramethylbenzidine (TMB), 2,2'-azino-di[3-ethylbenzothiazoline sulphonate] (ABTS), o-dianisidine, 4-chloronaphthol (4-CN), nitrophenyl-β-D-galactopyranoside (ONPG), o-phenylenediamine (OPD), 5-bromo-4-chloro-3-indolyl-β-galactopyranoside (X-Gal), methylumbelliferyl-β-D-galactopyranoside (MU-Gal), p-nitorphenyl-α-D-galactopyranoside (PNP), 5-bromo-4-chloro-3-indolyl-β-D-glucuronide (X-Gluc), 3-amino-9-ethyl carbazol (AEC), fuchsin, iodonitrotetrazolium (INT), tetrazolium blue and tetrazolium violet.

One type of detectable conjugate is a covalent conjugate of an antibody and a fluorophore. Directing photons toward the conjugate that are of a wavelength absorbed by the fluorophore stimulates fluorescence that can be detected and used to qualitate, quantitate and/or locate the antibody. Some examples described herein are based on semiconductor nanocrystals (also referred to as quantum dots or QDots). Quantum dot bioconjugates are characterized by quantum yields comparable to the brightest traditional dyes available. Additionally, these quantum dot-based fluorophores absorb 10-1000 times more light than traditional dyes. Quantum dots typically are stable fluorophores, often are resistant to photo bleaching, and have a wide range of excitation, wave-length and narrow emission spectrum. Quantum dots having particular emission characteristics, such as emissions at particular wave-lengths, can be selected such that plural different quantum dots having plural different emission characteristics can be used to identify plural different targets. Emission from the quantum dots is narrow and symmetric, which means overlap with other colors is minimized, resulting in minimal bleed through into adjacent detection channels and attenuated crosstalk, in spite of the fact that many more colors can be used simultaneously. Symmetrical and tunable emission spectra can be varied according to the size and material composition of the particles, which allows flexible and close spacing of different quantum dots without substantial spectral overlap. In addition, their absorption spectra are broad, which makes it possible to excite all quantum dot color variants simultaneously using a single excitation wavelength, thereby minimizing sample autofluorescence. A quantum dot is a nanoscale particle that exhibits size-dependent electronic and optical properties due to quantum confinement. Quantum dots have, for example, been constructed of semiconductor materials (e.g., cadmium selenide and lead sulfide) and from crystallites (grown via molecular beam epitaxy), etc.

A variety of quantum dots having various surface chemistries and fluorescence characteristics are commercially available from Invitrogen Corporation, Eugene, Oreg. (see, for example, U.S. Pat. Nos. 6,815,064, 6,682,596 and 6,649,138, each of which patents is incorporated by reference herein). A quantum dot can be coupled to a binding moiety selected for a target of interest. After binding to the target, the quantum dot can be detected based on, for example, its fluorescence characteristics, absorption characteristics, excitation characteristics or fluorescence lifetime.

While many examples of contrast agents conducive to multi-modal contrast imaging with multiplexed probes can be used, including tags based on quantum dots such as described above, tags configured for imaging mass spectrometry are also highly useful. These so-called "mass tags" can be configured for specific binding to one or more chemistries or molecules of interest; and subsequently detected using matrix assisted laser desorption ionization (MALDI) mass spectrometry or other mass spectrometry techniques. One or more mass tags can be applied to a specimen such as a tissue section that is to be evaluated or has been evaluated using refractive index contrast and/or fluorescence as described above. In one example, ligands or antibodies are selected for binding to a target molecule and are secured to gold nanoparticles or other nanoparticles. Ligands or antibodies that are present on the nanoparticle bind to the target protein. After binding to the target, the small molecules on a nanoparticle can be subsequently analyzed by laser desorption ionization time-of-flight mass spectrometry (LDI-TOF MS). U.S. Pat. No. 7,202,472 discloses representative nanoparticles having antibodies coupled thereto for specific binding to a target. Multiple analytes can be detected in this way by providing corresponding specific antibodies or ligands that are bound to respective nanoparticles, wherein typically each nanoparticle provides a different mass signature. In some examples, photocleavable mass tag-labeled antibodies such as described in US Patent Appl. Pub. 2009/0088332 can be used. In other examples, such disclosed in US 2002/0150927, a probe is coupled to a mass modifier, the mass modifier is cleaved using an enzyme, and the released mass modifier is detected. In other examples such as disclosed in WO 00/68434 which is incorporated herein by reference, liposome encapsulating specific binding oligos are provided, each having specific distinguishing masses separable by MALDI.

Representative Examples

In some additional examples, images of formalin-fixed, paraffin embedded histological tissue sections prepared according to Ventana Medical Systems (Tucson, Ariz.) protocols were obtained. In examples in FIGS. 4,5,6,10,12,13, 20, and 21, tissue sections were rendered from prostatectomy and processed for fluorescence in-situ hybridization (FISH) with semiconductor nanocrystal quantum dot (QDot) and counterstained with the fluorescent stain 4',6-diamidino-2-phenylindole (DAPI). QDot detection and DAPI fluorescence can be produced with an ultraviolet stimulus beam in a wavelength range of 370+/−20 nm Such a stimulus beam is well suited for simultaneous multiplex excitation of UV-absorbing nuclear counterstains such as DAPI as well as multiplexed QDot probes. Refractive index contrast in the example contrast scheme is bright against a dark field and does not depend on light absorbing stains and thus permits simultaneous viewing and recording of fluorescence contrast.

Figures 4A, 4B:
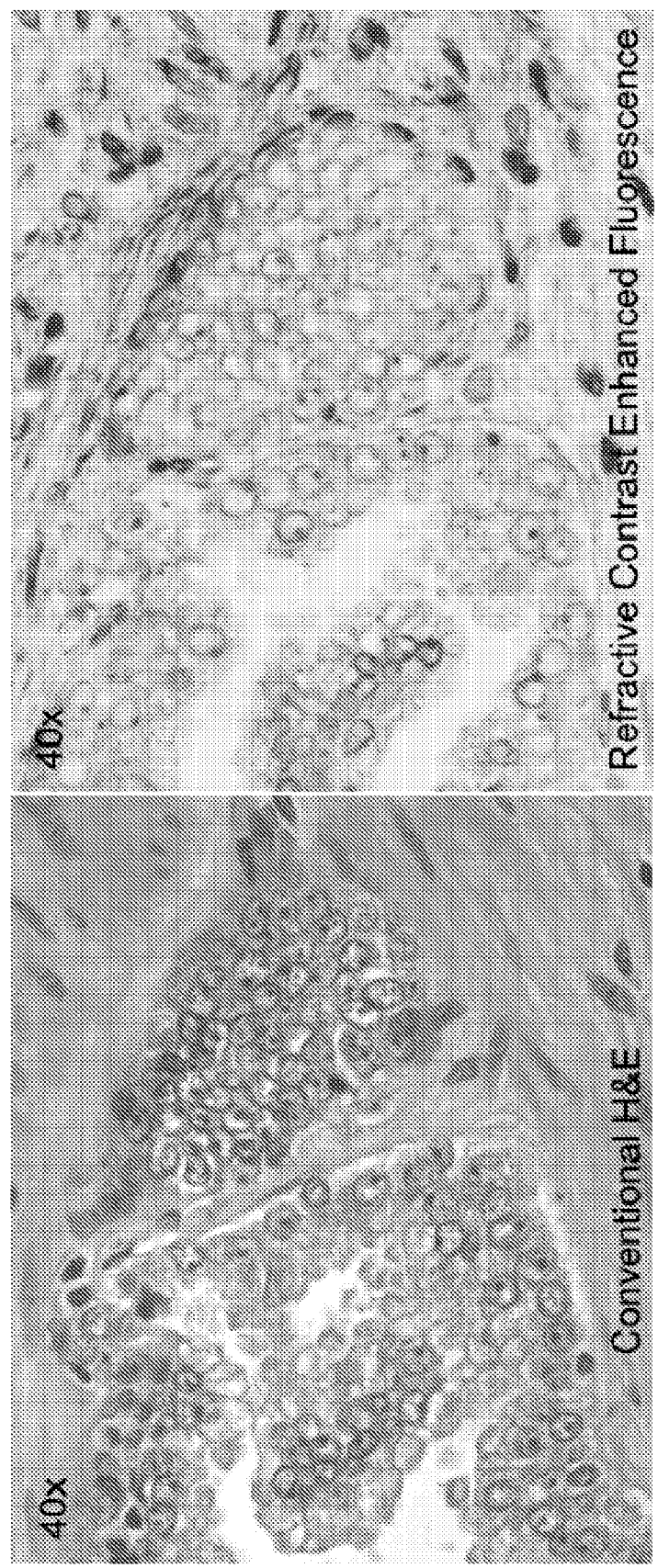
FIG. 4A is a representative conventional H&E stained image of a human prostate section.
FIG. 4B is a multiple mode contrast image of a human prostate section based on a combination of a dark field refraction image and a fluorescence counterstain image rendered in brightfield context.

Direct viewing of such specimens using a microscope system such as that of FIG. 1 was found to be useful for direct visualization using long pass (410 nm) filters installed directly in microscope eyepieces. The resulting viewed images contained nuclei that appeared blue among gold/silver histological structure. Additional color (for example, yellow or red) for direct viewing can be induced using one or more wavelength filters in the transmitted light path. The contrast provided by either illumination (fluorescence or transmitted dark field) can be conveniently shuttered to enable imaging with a single contrast method independent of the other. Light source intensities (stimulus beam, dark field illumination field) can be controlled so as to balance the contrast for direct two-color visualization or recording on a single sensor with a standardized integration time. A representative combined dark field (i.e., refractive)/fluorescence contrast image is shown in FIG. 4B in 2-color overlay and brightfield rendering along with an image of a serial section of the same specimen produced with a conventional H&E stain (FIG. 4A). The image of FIG. 4B is based on both a color LUT and image inversion. The type of data visible in the unstained tissue section (FIG. 4B) can be used in the diagnosis of prostatic intraepithelial neoplasia (PIN) and anomalous growth patterns present in prostate cancer (FIG. 20, FIG. 21) in a manner similar to that of the conventional H&E stained image (FIG. 4A), but also interrogated for molecular probe localizations as well. Moreover, the additional features, such as prominent nucleoli, are not apparent with DAPI fluorescence alone. Thus, such combined images and processing thereof can be useful in diagnosis and treatment, and can not only supply the same information as conventional stain based images, but also yield additional information.

Figures 5A, 5B, 5C, 5D:
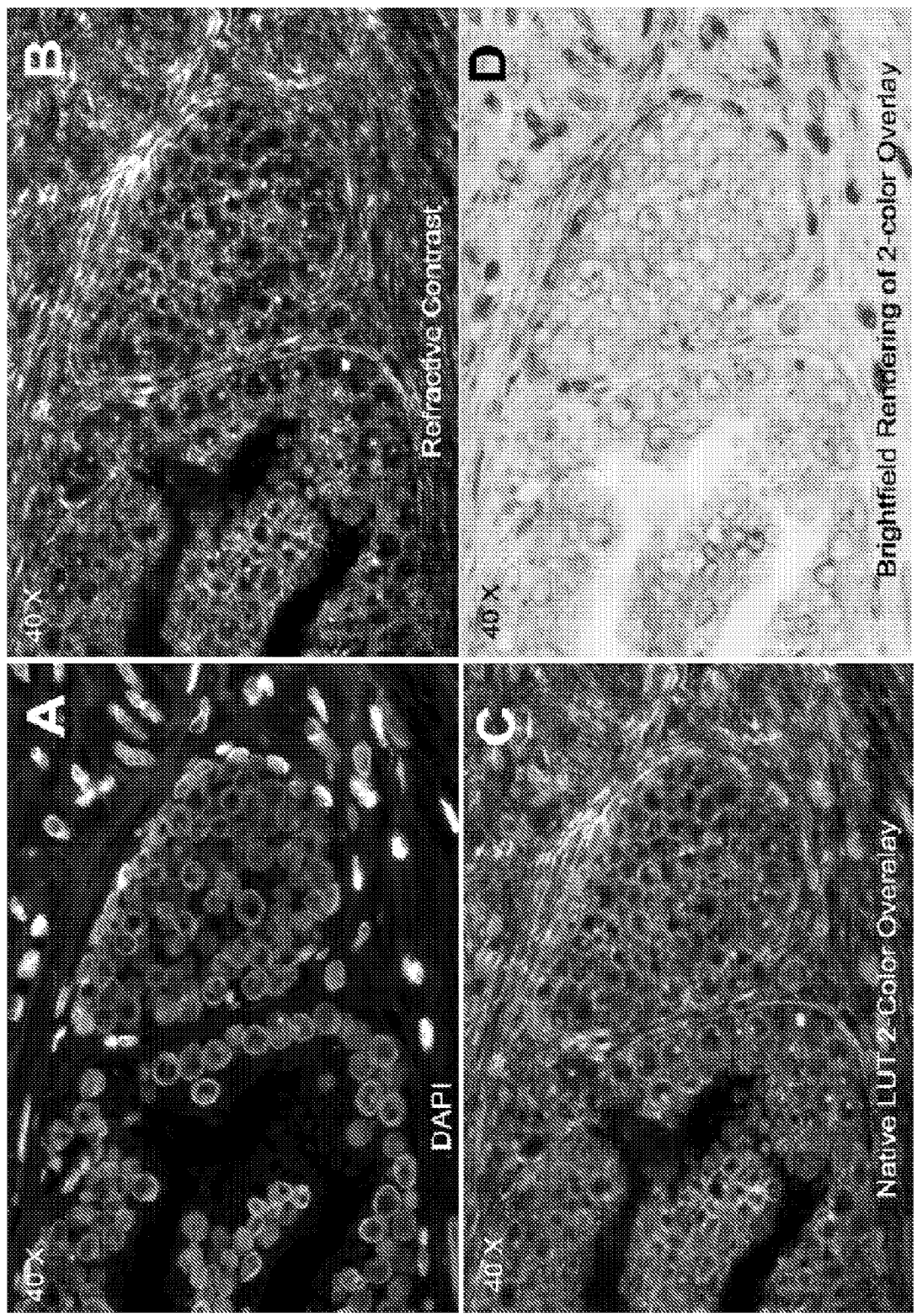
FIGS. 5A-5B are dual-illumination multiple mode contrast (refractive contrast and fluorescence) images recorded with a monochrome CCD with sequential exposures taken using interference filters to select either the blue DAPI fluorescence wavelengths (FIG. 5A) or the longer wavelength transmitted dark field wavelengths (FIG. 5B).
FIG. 5C is a pseudo-color image obtained by application of inverted color lookup-tables for pseudo-color to the images of FIGS. 5A-5B and adding the inverted color images.
FIG. 5D is a pseudo-colored, bright field rendering of the image that corresponds to the image of FIG. 5C after inversion of the mapped color space.
Figure 6:
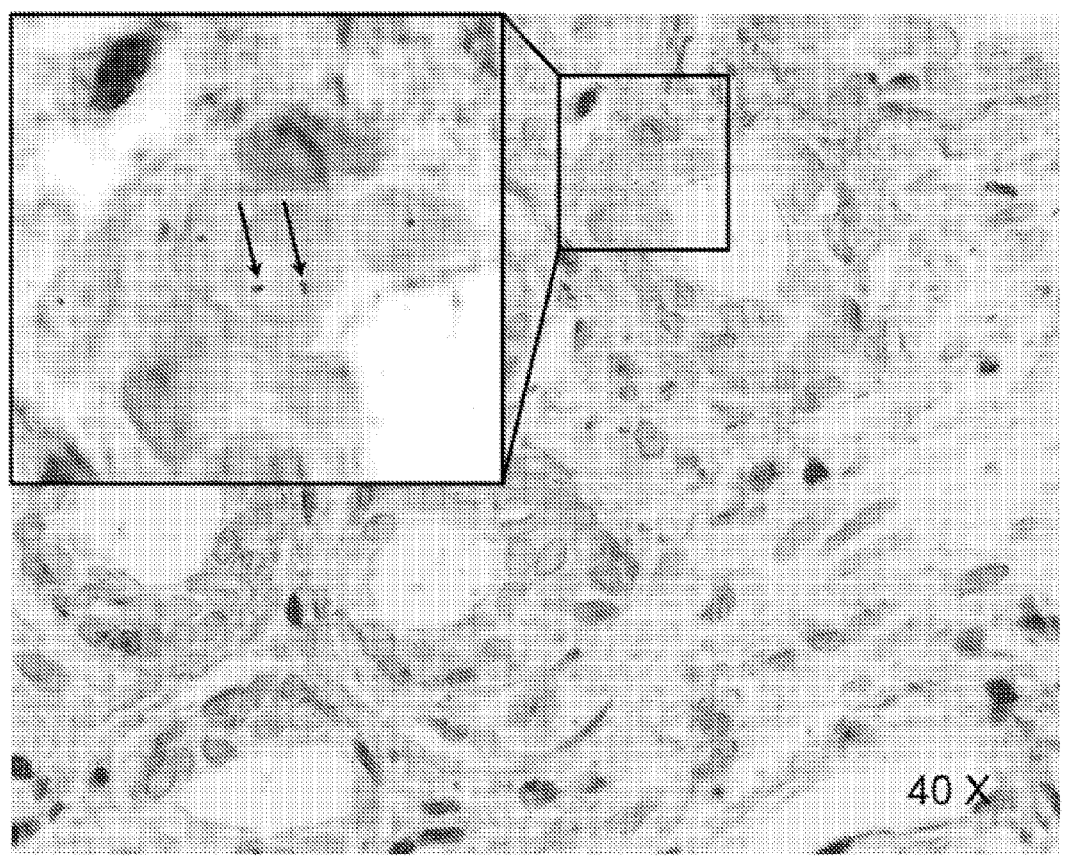
FIG. 6 is a brightfield context rendering image by overlaying localizations of quantum dot fluorescent probes with peak emission wavelengths of 565 nm and 655 nm from a DAPI counter-stained formalin-fixed, paraffin embedded sample also imaged for refractive contrast.

In these examples, dual-contrast (refraction-dark field and fluorescence, respectively) images were recorded with a monochrome CCD with sequential exposures taken using interference filters to select either blue DAPI fluorescence wavelengths or longer wavelength refraction contrast light flux. FIG. 5A is a monochrome image using DAPI fluorescence, and FIG. 5B is a monochrome image obtained of refraction contrast w/ darkfield illumination. Additional images based on combinations of the images of FIGS. 5A-5B are shown in FIGS. 5C-5D. FIG. 5C is a pseudo-color image obtained by overlaying the monochrome images of FIGS. 5A-5B and applying a pseudo-color mapping based on contrasting color lookup tables (LUTs). FIG. 5D is an image that corresponds to the image of FIG. 5C after inversion of and coloring of the image of FIG. 5C. The image of FIG. 5D can be referred to as a "bright field rendering" of the image of FIG. 5C.

Figure 18:
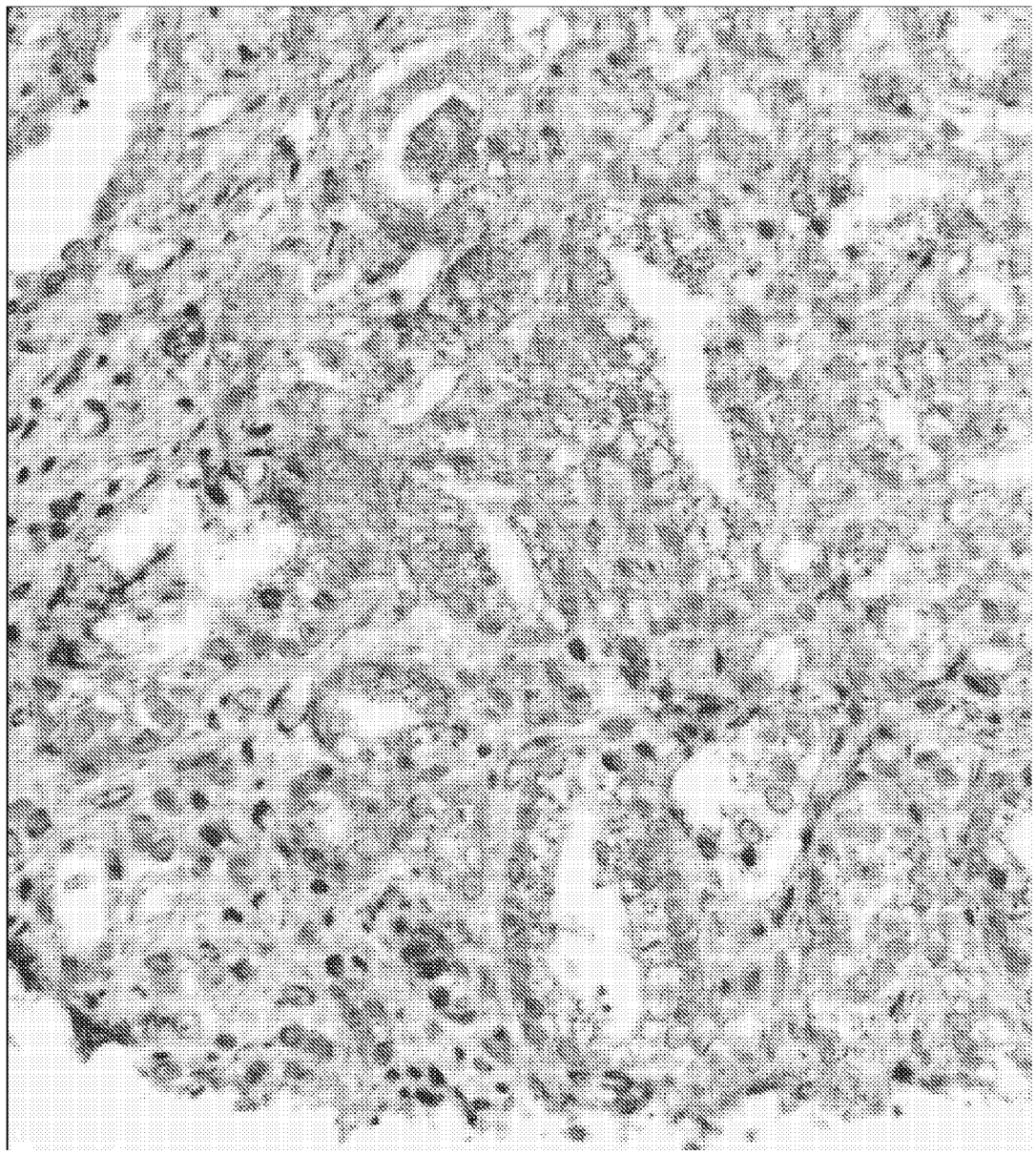
FIG. 18 is a representative image of a prostate cancer imaged using dual-mode contrast and presented in brightfield context at 20× magnification for pathology determination. Prominent nucleoli and anomalous growth patterns characteristic of prostate cancer are evident.

As discussed above with reference to FIG. 2, multiple fluorescence images can be obtained and combined. The ability to localize and render DNA sequence specific probes using a pseudo bright field method was tested using the 3'5' ERG break-apart probe in the context of an ERG gene break-apart FISH assay on DAPI counterstained prostate tissue prepared according to the steps outlined in FIG. 18. The ability to apply pseudo-color lookup tables to the probe intensity levels and overlay in an additive color scheme prior to inversion was found to generate sufficient contrast to identify at least two fluorescent probes simultaneously with the refractive contrast and DAPI counterstained image rendered in pseudo-brightfield. Sequential acquisitions of QDot probe localizations at 565 nm and 655 nm were obtained from a DAPI stained sample and processed to produce an image shown in FIG. 6 along with refractive contrast and fluorescence of the DAPI counterstain. As shown in the insert to FIG. 6, such acquisitions permit brightfield rendering and display of dual-probe FISH localizations (see arrows directed to green and red areas corresponding to probe localizations at 565 nm and 655 nm, respectively). In this case, the probe intensities are overlaid onto the pseudo-color, pseudo-bright field refractive index/DAPI contrast image. Thus, image features similar to those obtained with conventional H&E stains can be viewed, along with additional molecular chromosome rearrangements revealed by QDot probes. The overall appearance is familiar to those accustomed to H&E stained images, and little or no retraining is needed to permit clinicians to comfortably evaluate specimens based on these images.

Figure 7:
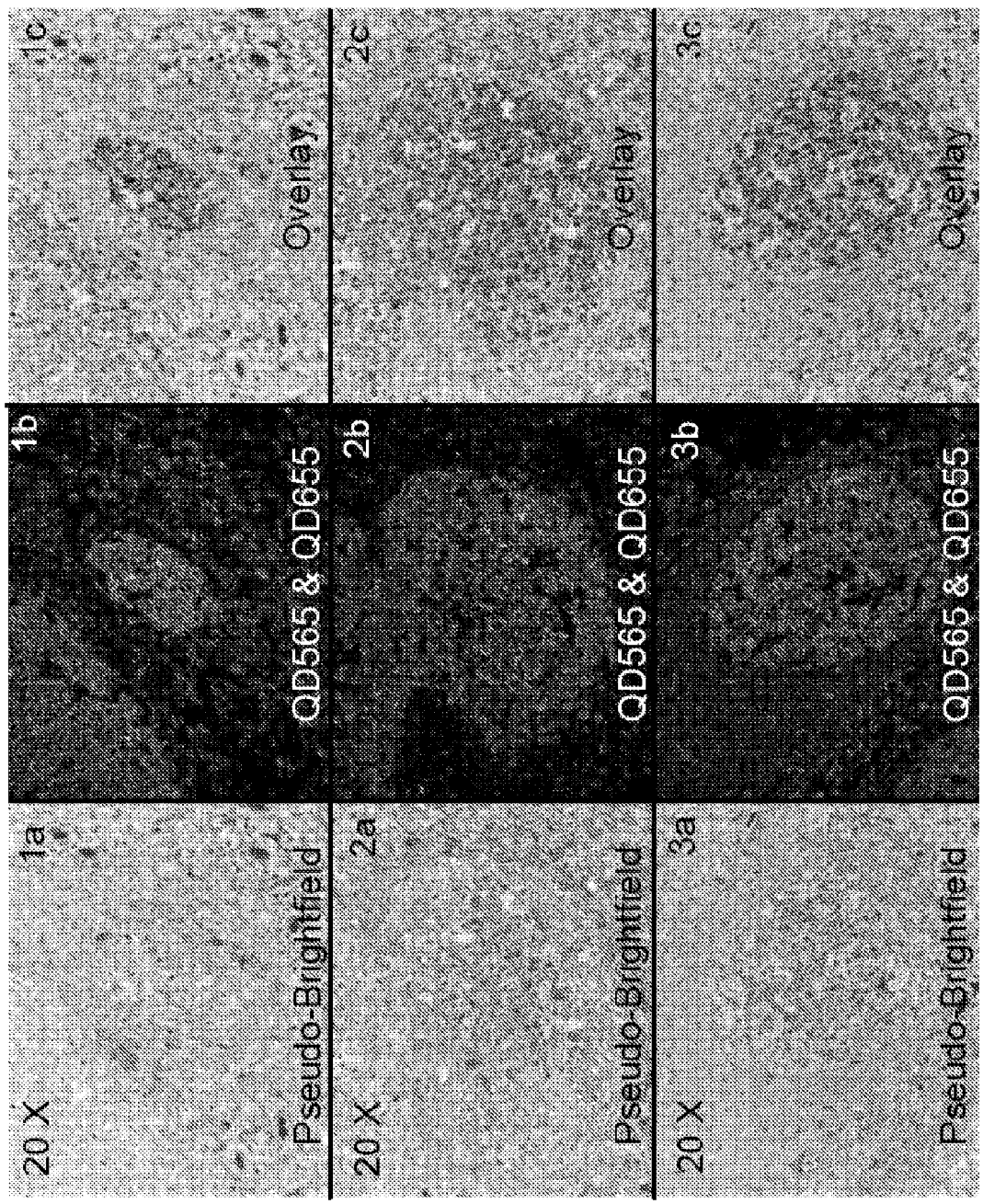
FIG. 7 contains other example images of multimode imaging for brightfield context display. Dark field refractive contrast images and DAPI fluorescence images of DAPI counterstained tonsil sections were obtained, overlaid, and rendered as color bright field images as shown in FIG. 7 (1a-3a). Protein-specific immuno-probes (localized in fluorescence using quantum dots having peak emissions at 565 nm for CD20 antigen and 655 nm for Ki67 antigen) were applied to the DAPI counterstained tonsil sections to produce corresponding immuno-probe fluorescence based images. The probe images were overlaid in contrasting pseudo-colors (red and green) as shown in FIG. 7 (1b-3b).

In another example, protein-specific immuno probes (QD565 for CD20 antigen and QD655 for Ki67 antigen) were applied to DAPI counterstained tonsil tissue sections to produce images as shown in FIG. 7. The generalized processing steps used for tissue processing and contrast optimization are outlined in FIG. 18. Dark field refraction images and DAPI fluorescence based images were obtained, overlaid, and rendered as pseudo-color pseudo-bright field images as shown in FIG. 7 (1a-3a) Immuno-probe fluorescence based images were obtained for each probe detection and overlaid together as a fluorescence image in contrasting colors as shown in FIG. 7 (1b-3b). As shown in FIG. 7(1b-3b), the probe localization images for the QD565 and QD655 probes were pseudo-colored in green and red, respectively. The images of FIG. 7(1a-3a) and FIG. 7(1b-3b) were combined to produce the images final images thereby revealing the probe localizations on tissue structure context FIG. 7(1c-3c).

Figure 8:
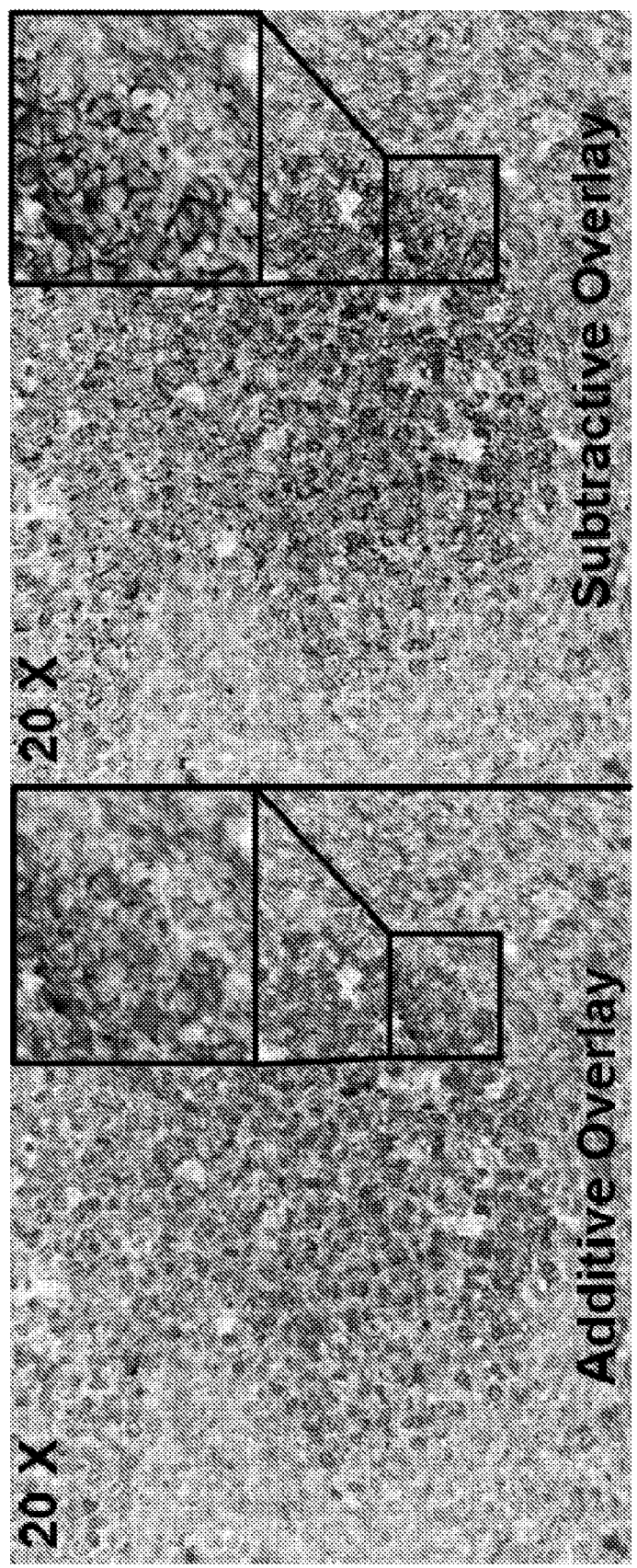
FIGS. 8A-8B are additional representative images in which simulated brightfield histological images are obtained, and fluorescent probe images combined using alternative methods.

Further examples illustrate two methods for overlaying probe localization on brightfield context. FIG. 8A is an additive overlay of a pseudo-bright field image with fluorescent probe images using QD565 and QD655 probes on the DAPI counterstained specimen used in obtaining the images of FIG. 7. FIG. 8B is a subtractive overlay in which probe image color maps are subtracted from the pseudo H&E image. Subtractive overlay may more closely approximate images obtained with light absorbing stains, and be advantageous in contrast generation and multiplexed image overlay.

Figure 19:
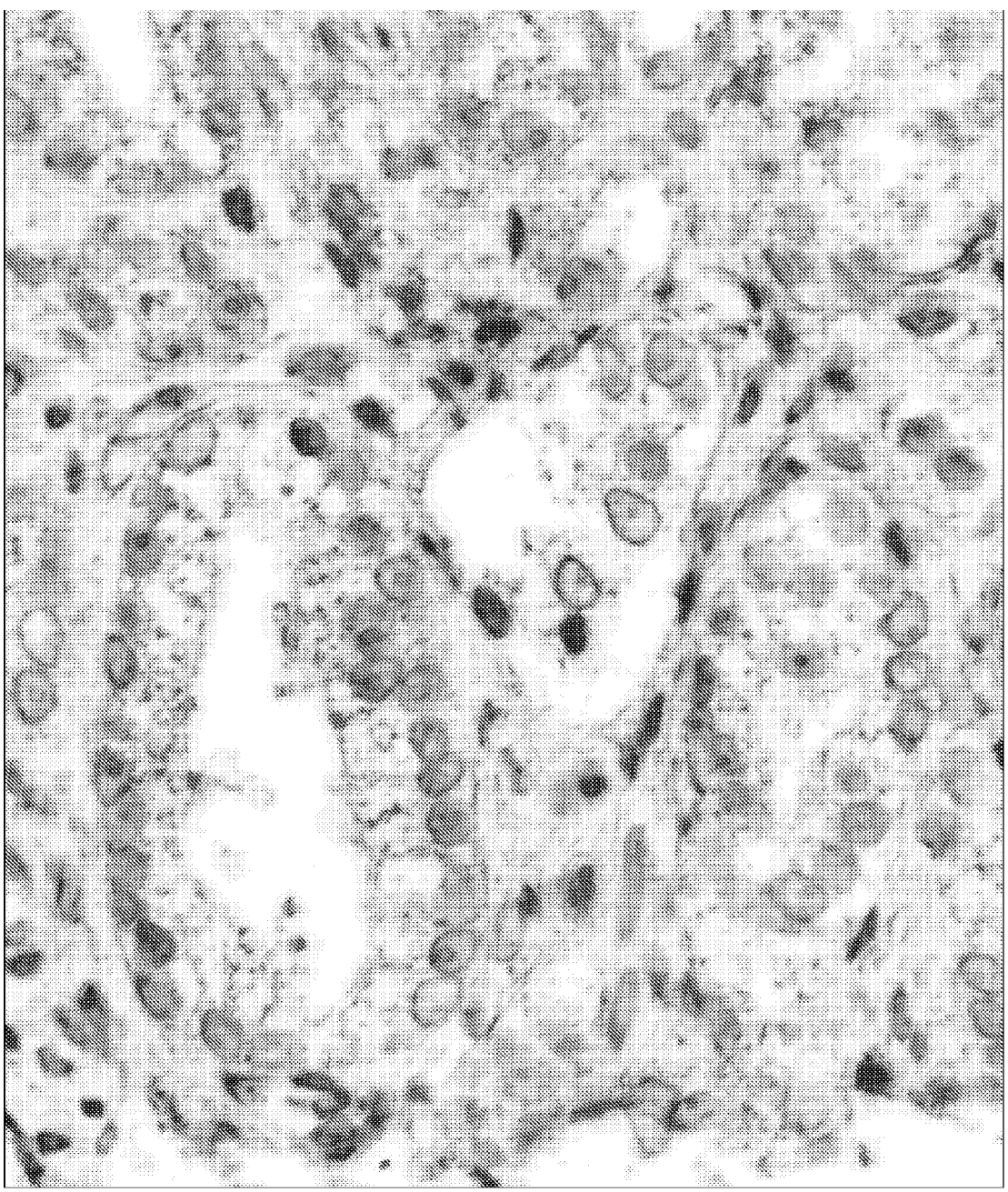
FIG. 19 is a portion of the same region imaged at 40× magnification using the same simultaneous dual-mode method of combining refraction contrast with fluorescent nuclear counterstain and rendering in brightfield context.

In another example, mRNA-specific ISH probes (QD605 for 18s ribosomal RNA and QD625 for HER2 mRNA) were applied to DAPI counterstained Calu-3 xenograft tissue sections to produce images as shown in FIG. 19. The generalized processing steps used for tissue processing and contrast optimization are outlined in FIG. 18. Dark field refraction images and DAPI fluorescence based images were obtained, overlaid, and rendered as pseudo-color pseudo-bright field images as shown and fluorescence based images were obtained for each probe detection and combined together with the brightfield context rendering. As shown in FIG. 19, the probe localization images for the QD605 and QD625 probes were pseudo-colored in cyan (black arrow) and black (green arrows), respectively. The final image of FIG. 19 thereby reveals the probe localizations on tissue structure context.

Figure 12:
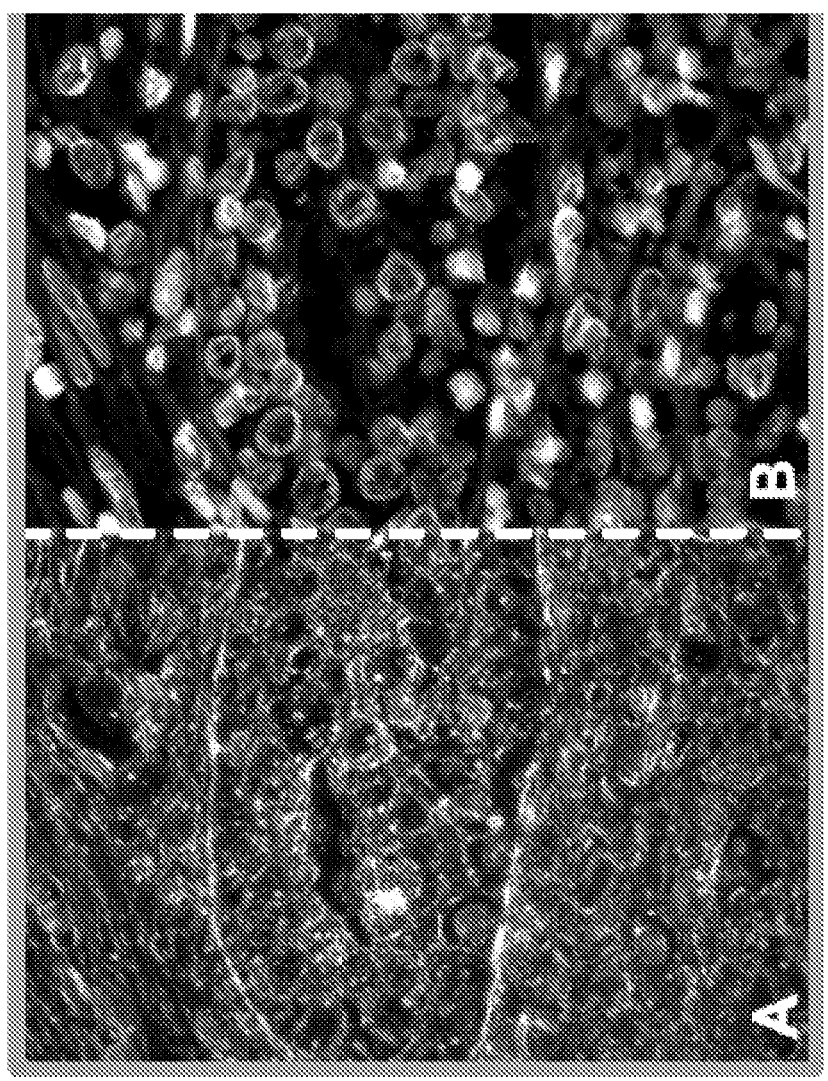
FIG. 12 contains a side-by-side refractive index (dark field) image (A) and a DAPI image (B) of the same tissue section acquired and displayed simultaneously.

To demonstrate video rate imaging, a 2-color imaging method was tested using an imaging beamsplitter similar to that outlined in FIG. 11 to separate DAPI emission wavelengths from longer wavelength refraction contrast and project the two wavelength components of the exact same field of view side-by-side on a single monochrome CCD sensor. Using a secondary beamsplitter permits simultaneous image acquisition of two color channels and streaming to a computer display as well as streaming recording of rapid time lapse sequences limited only by the required integration time and readout time of the camera. FIG. 12 contains a side-by-side refractive index (dark field) image (A) and a DAPI image (B) of the same tissue section acquired simultaneously.

Figure 13:
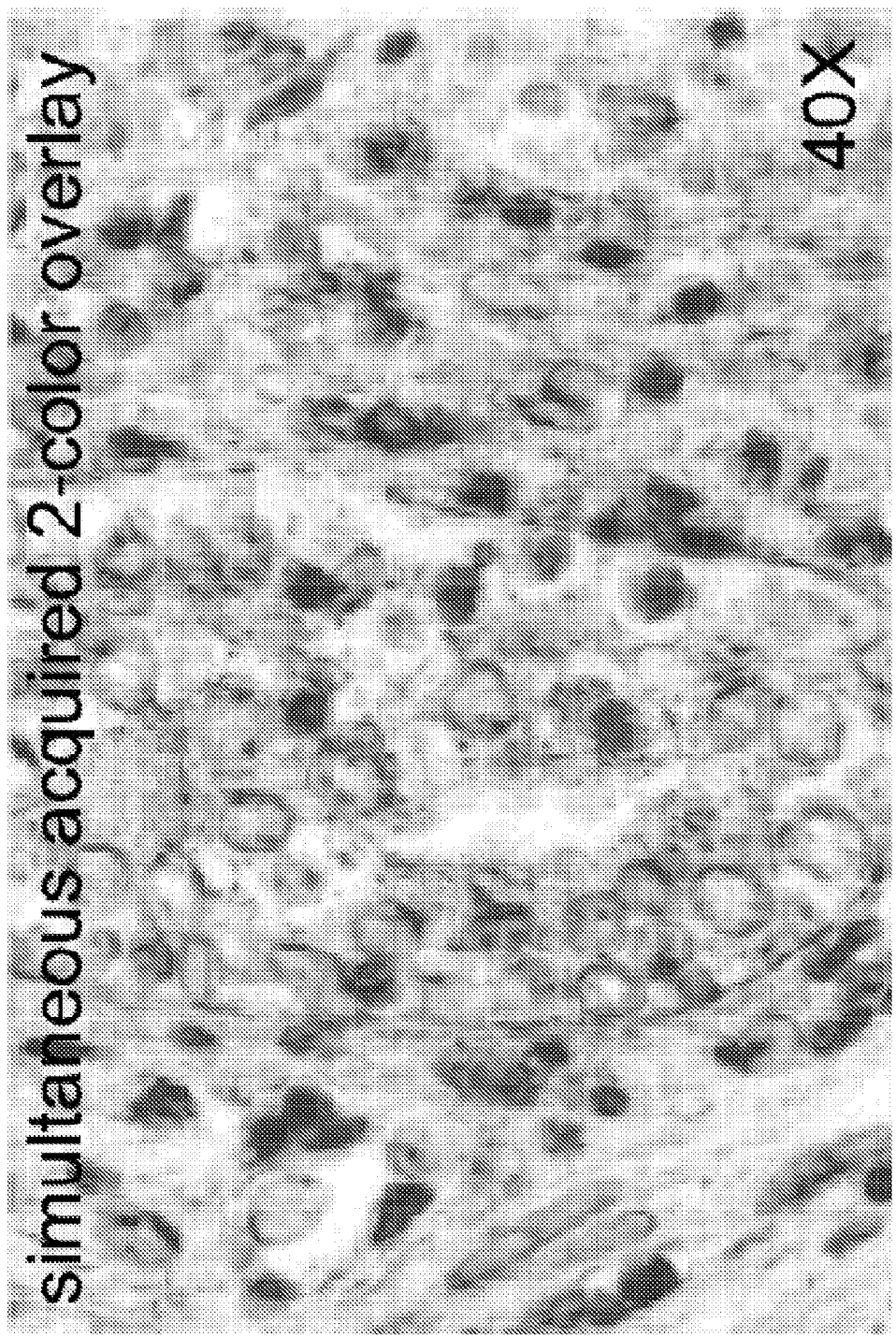
FIG. 13 contains a two color brightfield rendering overlay image (with pseudo-color and image inversion) based on the side-by-side images of FIG. 12. Note this image is rotated with respect to the FIG. 12 image.

The use of monochrome intensity capture of distinct wavelength bands used to produce complementary multiple mode images permits convenient application of specialized lookup tables to the individual grey-scale intensity images for a DAPI counterstain, the transmitted dark field image, and one or more probe localizations. A method which maps the lowest pixel intensities to white in RGB space and the brightest pixels to full saturation of a given hue was tested in the context of acquisition of streaming images. This alternative rendering of the transmitted dark field image can be navigated in real time at various magnifications and snapshot images may be recorded at will. FIG. 13 contains a two color overlay (with pseudo-color and image inversion) based on the side-by-side images of FIG. 12. (Note this image is rotated with respect to the FIG. 12 image.) Such images can be produced and overlaid rapidly, permitting a perception of 'live' color brightfield viewing of tissue structure and counterstain. This approach can be extended to live probe overlay using multiple sensors or by dividing light into multiple wavelength bands for projection on different areas of a single sensor or combinations of multiple sensors with multiple wavelengths projected on one or more sensors. Dark field refraction and fluorescence images may alternatively be recorded using sequential detection filters, sequential illumination, by using a spectral imaging device as described in Malik et. al. 1996, Hoyt et. al. 2002, both of which are incorporated herein by reference, or by using a single shot Bayer-mask color camera.

Figures 14A, 14B:
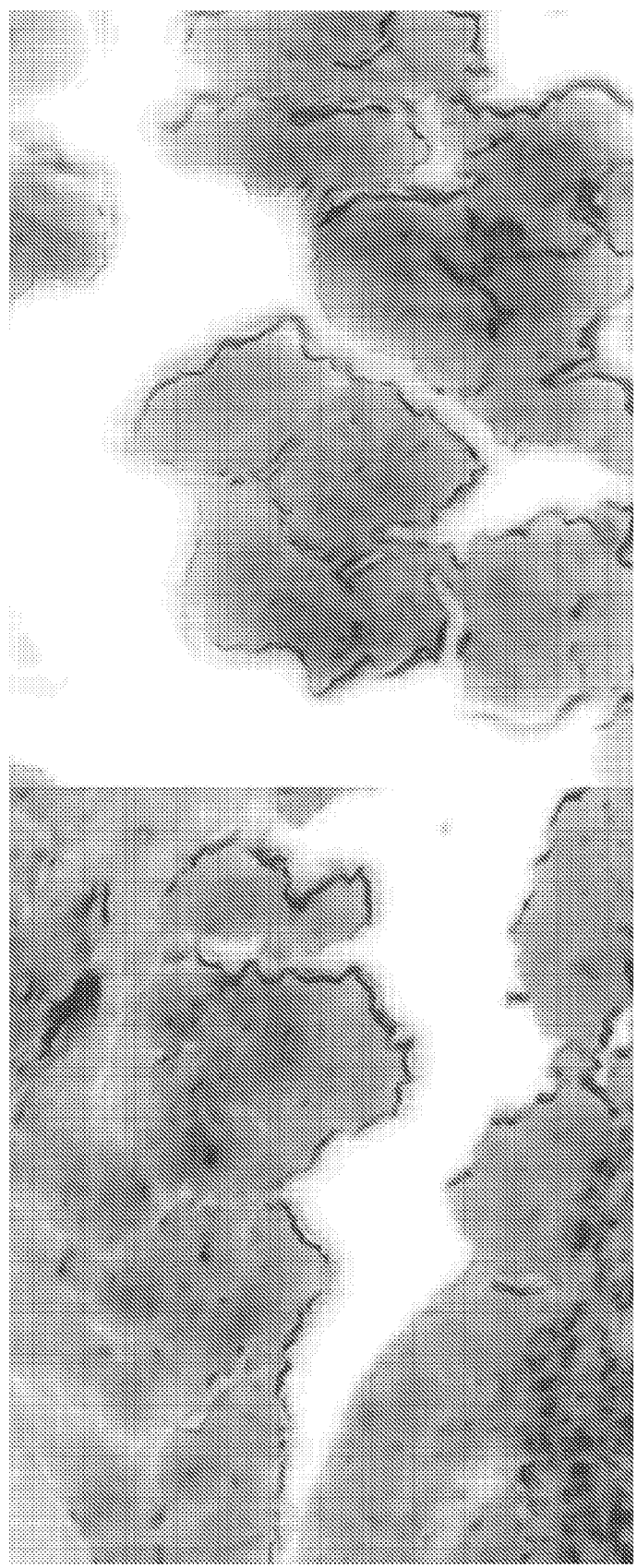
FIGS. 14A-14B are images of cryosectioned mouse kidney tissue specimens prepared for deposition of mass spectroscopic imaging tags. Contrast is produced by refraction at tissue edges and tissue autofluorescence (blue).
Figures 15A, 15B:
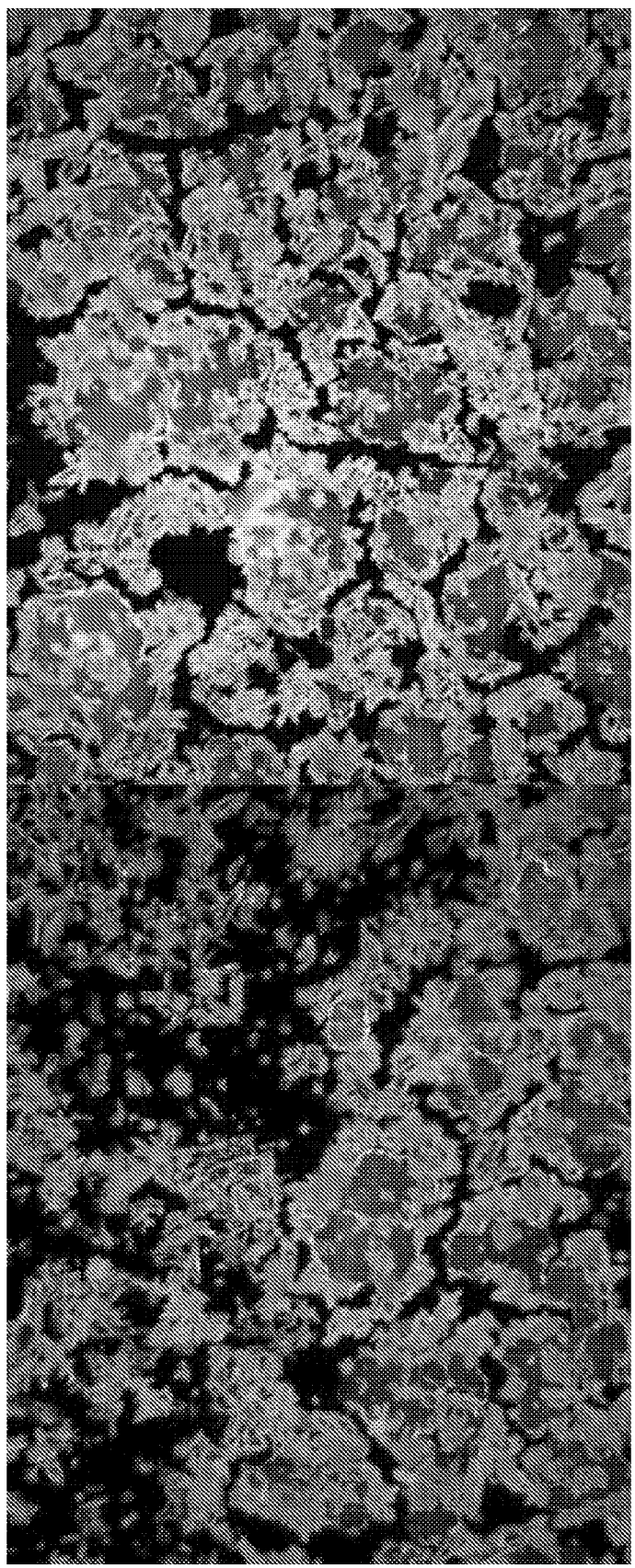
FIGS. 15A-15B are images of mouse kidney tissue specimens prepared for mass spectroscopic imaging by deposition of an ionizing matrix. Autofluorescence appears blue and refractive index contrast associated with ionizing matrix crystals is apparent.

While optical based contrast using refractive index, fluorescence, or other methods (FIG. 22) can be used in the microscope systems of FIG. 1 and FIG. 11, specimens evaluated in this way can also be prepared for further analysis using mass tags in mass spectrometry. In a representative example, uncoated and matrix-coated mouse kidney tissues were prepared using a standard mass spectrometry imaging protocol. Nuclear counterstain was not used but it was possible to image gross section morphology and tissue presence based on refractive index differences at tissue edges and by detecting autofluorescence using a fluorescence detection optical subsystem. Representative sections are illustrated in FIG. 14. Refraction at bare tissue edges causes the edges to appear bright, and blue autofluorescence is associated with the tissue itself. FIG. 15 contains images illustrating combined dark field/autofluorescence images of the mouse kidney tissues after deposition of an ionizing matrix for mass spectrometry. Matrix crystals appear yellow, and autofluorescence appears blue. These images show that dark field and fluorescence images can be obtained, even after application of the ionizing matrix.

Additional Discussion

Dark field refractive index contrast and fluorescence have been used simultaneously in some disclosed examples so as to produce images with multi-modality contrast in tissue samples stained with a fluorescent nuclear counterstain. This approach is useful in the use of multiplexed molecule specific probes for IHC, FISH, and mRNA-ISH, with QDot detection, on the same tissue section, for purpose of determination of pathological condition, and may also be used to image tissues prepared for imaging mass spectrometry. This multi-modality contrast scheme has been demonstrated to provide complimentary structural context information in a manner analogous to routine histological brightfield stain/counterstain combinations such as H&E. The structures visible through refractive index contrast include protein moieties, and such images permit visualization of structural anomalies and growth patterns of known pathological significance; including structures such as nucleoli, extracellular matrix, and cell and nuclear membranes. Under fluorescence illumination alone such structures are not apparent. Particular structures visualized using refractive index/fluorescence contrast provide a context for observation of molecular probe signals on the same tissue section and will aid physicians in the screening of tissues and diagnosis of pre-cancer and cancer disease states. Dark field refractive index contrast is particularly useful in that the approach provides bright features against a dark-field and does not use light absorbing stains. Thus refraction contrast is compatible for direct combination with multiplexed fluorescent emitting probes used for localization of cancer markers on transparent tissue sections prepared using specialized tissue fixation, embedding and staining protocols. This method does not interfere with probe chemistry or quantitation when combined with quantitative spectral imaging of QDot probes. By restricting the illumination wavelength for refraction-contrast to a wavelength that is red-shifted from probe emission, the illumination methods can be used simultaneously in the context of spectral image data acquisition of multiplexed probes. Refraction-contrast combined with fluorescence also permits imaging tissue context and pathological state on transparent tissues intended for imaging mass spectrometry.

The combined contrast methods (refraction contrast and fluorescence) may be visualized directly through the eyepieces simultaneously in contrasting color. Furthermore, the 2-color image data can be recorded and/or displayed directly in a streaming fashion for real-time output and convenient snapshot recording of fields of interest. The use of simultaneous multi-wavelength acquisition on a monochrome camera provides a convenient means to apply specialized color lookup tables to the streaming grey-scale intensity images for the dark field refraction image and a fluorescent nuclear counterstain image. The application of CIEL*a*b* lookup tables corresponding to known color values preferred by physicians in the context of particular tissue types further refines the presentation of tissue structure to the practicing physician. Taken together, careful tissue processing, multi-modal contrast acquisition and image data processing can provide information similar to that which can be derived from conventional hematoxylin and eosin (H&E) stained tissue sections. Such images can also be combined with probe based image data associated with intranuclear, cytoplasmic and extracellular genetic, mRNA expression and protein antigen markers and other specific probes on otherwise unstained human tissue. By use of suitable color mappings and image inversions, image data may be presented and displayed to a trained pathologist in a familiar manner, and optically active or chemically resolvable data from the same field of view, such as mass spectral data, may be overlaid onto this familiar context.

Conclusion

As described above, multiple modality contrast can be preserved, enhanced and revealed in cells and tissue. These contrast elements can be combined and rendered to produce images similar to those produced with wavelength absorbing stains viewed under transmitted white light illumination. Multimodal contrast images make use of various optical and chemical characteristics incorporated into tissue through specialized processing. The contrasted components can be effectively segmented and presented digitally using engineered color schemes based on classical contrast methods historically used to reveal the same anatomical structures and histochemistry, thereby providing relevance to medical training and experience. The resulting structural context can be used for pathology determination and also to provide context for multiplexed molecular and chemical markers. This approach provides important correlative information that may otherwise be difficult or impossible to obtain. In some examples, dark-field contrast derived from refractive index and fluorescent DAPI counterstain images are combined to produce images similar to those obtained with conventional H&E staining. These multi-modal data images have been shown to be useful in pathology interpretation of the tissue sections. In addition, such multi-modal image data can be streamed to monitor to permit live navigation of histological samples. In other examples this structural context is subsequently combined with molecular localizations of genetic DNA probes (FISH), sites of mRNA expression (mRNA-ISH), and immunohistochemical (IHC) probes localized on the same tissue sections. Multi-modal contrast may also used to evaluate and map tissue sections prepared for mass spectrometry.

Although refractive contrast is a convenient example, other methods are suitable as well. Table 3 below lists contrast modalities that may be used to produce complimentary information that can be combined to provide useful tissue structural context combined with molecular information for pathology determination. Table 4 lists principle phases of automated tissue preparation used for molecular labeling of immunocytochemical, DNA and mRNA probes on tissue. The details of these standardized phases impact optical and chemical qualities that permit multiple mode imaging for pathology determination.

TABLE 3

Imaging Modalities Pertinent to Generating Complimentary Contrast in Tissue for Pathology Determination

| Modality | Tissue Contrast Factor |
| --- | --- |
| Brightfield microscopy | Use of absorbance and scattering properties of tissue or chemical/molecular markers |
| Darkfield (refraction) microscopy | Use of Refractive Index and scattering properties of tissue or chemical/molecular markers |
| Continuous Wave Fluorescence Intensity (fluorescence microscopy) | Use of wavelength resolved fluorescence emission to image map fluorescent molecules |
| Multiphoton non-linear fluorescence intensity microscopy | Use of wavelength resolved fluorescence emission to image map fluorescent molecules with 2-photon absorption cross section |
| Total Internal Reflectance Fluorescence Microscopy (TIRFM) | Use of excitation light at numerical aperture exceeding the critical angle to create evanescent wave that excites fluorescent molecules only in near proximity to the coverslip interface |
| Chemiluminescence Imaging | Chemical luminescence of chemical marker or tissue chemistry |
| Resonant Energy Transfer Imaging | Non-emitting (dark) transfer of excited state from one fluorescent molecule (donor) to another (acceptor) in close proximity |
| Excitation Ratio Imaging | Imaging the Ratio of fluorescence emission intensities at different excitation wavelengths |
| Emission Ratio Imaging | Imaging the Ratio of different fluorescence emission intensities at single excitation wavelength |
| Polarization Microscopy | Imaging Contrast produced by polarizing optical activity of tissue or probe |
| Birefringence Polarization Microscopy | Imaging Contrast produced by birefringent activities of anisotropic crystals in the specimen |
| Fluorescence Lifetime Imaging | Temporally resolved imaging excited state lifetimes of fluorescent molecules |
| Interference Contrast | Rate of change of phase shift due to changes in refractive index in prepared tissue |
| Phase Contrast | Amplitude of phase shift due to changes in refractive index in prepared tissue |
| Harmonic Generation | Frequency doubling or tripling of excitation source by molecular organization in tissue or the use of specialized probes |
| Imaging Raman Spectroscopy | Chemical spectral map imaging in which inelastic scattering depends on vibrational and rotational molecular states of constitutive molecules or markers |
| Imaging FTIR Spectroscopy | Chemical spectral map imaging in which absorbance of organic chemical bonds in markers or constitutive molecules provides information about sample composition |
| Imaging Mass Spectroscopy | Chemical spectral map imaging in which chemical composition is determined using mass and charge properties of constitutive molecules or markers |
| Polarization Anisotropy Imaging | Imaging degree of preservation of polarization state or degree of depolarization from emitted, transmitted or reflected light |
| Stochastic Photoactivation Optical Reconstruction (PALM, STORM) | Use of photoswitchable markers or stochastic blinking to determine structure, generally used in a fluorescence context |
| Structured Illumination Reconstruction Imaging | Use of patterned illumination to resolve details, generally used in a fluorescence context |
| Stimulated Emission Depletion Microscopy | Use of optical masking to permit de-excitation of fluorescent molecules to enhance resolution |
| 4Pi Microscopy | Use of interference between multiple excitation beams to enhance resolution in generation of fluorescence signal |
| Optical Coherence Tomography | Use of broad-band frequency light in an interferometric tomography method that identifies scattering and reflective interfaces through a volume on a microscopic scale |
| Near Field Scanning Optical Microscopy | Use of a physical nano-scale optical probe to limit excitation by means of evanescent waves from a sub-resolution aperture scanned in close proximity to the sample surface |
| Atomic Force Microscopy | Use of a nano-scale physical probe to scan topographic, mechanical and electromagnetic properties at the sample surface |
| Scanning Electron Microscopy | Use of a scanned electron beam to image surface topography and molecular markers below the diffraction limit of light. |
| Transmission Electron Microscopy | Use of transmitted electron beam to image tissue ultrastructure and molecular markers below the diffraction limit of light |

TABLE 4

Principle Phases of Automated Tissue Preparation

| Immunohistochemistry (IHC) | DNA Fluorescence In-Situ Hybridization (FISH) | mRNA Fluorescence In-Situ Hybridization (mRNA-ISH) |
|---|---|---|
| 1. Pre-Analytical Phase: Tissue Conservation | 1. Pre-Analytical Phase: Tissue Conservation | 1. Pre-Analytical Phase: Tissue Conservation |
| 2. Antigen Retrieval Phase: Assurance of Target Antigen accessibility | 2. Pre-Hybridization Phase: Assurance of Target DNA accessibility | 2. Pre-Hybridization Phase: Assurance of Target DNA accessibility |
| 3. Antibody Binding Phase: Target Antigen identification with antibody probes | 3. Hybridization Phase: Target DNA identification with DNA probes | 3. Hybridization Phase: Target DNA identification with DNA probes |
| 4. Post Binding Phase: Removal of non-specific background labeling | 4. Post Hybridization Phase: Removal of non-specific background labeling | 4. Post Hybridization Phase: Removal of non-specific background labeling |
| 5. Detection Phase: Addition of contract-generating visualization markers | 5. Detection Phase: Addition of contrast-generating visualization markers | 5. Detection Phase: Addition of contrast-generating visualization markers |
| 6. Post Detection Phase: Final tuning of optical quality and preservation | 6. Post Detection Phase: Final tuning of optical quality and preservation | 6. Post Detection Phase: Final tuning of optical quality and preservation |

Using such contrast modalities, diagnostic methods include providing two or more modalities of contrast to features of medical diagnostic relevance in tissue, wherein the two or more modalities of contrast provide complimentary correlative information, and the two or more modalities provide contextual information pertaining to tissue-level structure, anatomy or morphology. Typically, images associated with the two or more modalities of contextual context are rendered in a manner consistent with medical training and familiar to medical professionals (e.g. pseudo-H&E). Such images (prior to, during, or after rendering) can be recorded simultaneously or serially, and streamed to render on display to permit live visualization of the tissue for navigation. In some examples, two or more independent illumination paths are used. In other examples, transmitted darkfield refraction contrast images are acquired or processed simultaneously with incident light fluorescence contrast. In some applications, darkfield refraction contrast is segmented by restricting wavelength of light used. In other examples, incident light fluorescence contrast is used simultaneously with transmitted darkfield contrast.

In some examples, complementary contrast images are provided for direct viewing in two or more colorized components through eyepieces or are directed to a display. In some cases, it is convenient to acquire two or more complimentary contrast components in single acquisition and to simultaneously record complimentary components of multiple illumination paths in single spectral acquisition. In some examples, complimentary components are recorded by simultaneously wavelength segmenting and splitting the optical path.

In other examples, complimentary contrast components are rendered to provide a histological-stain brightfield context, typically based on color maps generated from physician preference of light-absorbing stain slides. In some examples, eosin-like color maps are used for refractive imaging of eosinophilic protein moieties. Typically, eosin color maps are applied, followed by image inversion. Additionally, hematoxylin-like color map for fluorescence DAPI imaging of nucleic acid moieties can be used, followed by image inversion. These and other complementary contrast components can be colorized and streamed. Inverted eosin color maps and inverted hematoxylin color maps can be provided, and combined images displayed in a brightfield context.

Spatially registered probe localizations and chemical maps can be overlaid on structural brightfield context, and probe localizations can be assigned colors for viewing probe localizations and chemical maps on structural brightfield context. Imaging modalities, color lookup tables, inversions, and specimen preparation can be configured to provide a selected image appearance based on pathologist preferences. Physical, optical and chemical tissue section preparation protocols can be configured in accordance with multiple mode imaging strategy. Multiple optical magnifications can be used with the same darkfield refraction illumination settings, and multimodal image contrast can be used to provide structural context for subsequent MALDI-TOF mass spectrometric imaging The above disclosure and the examples contained therein are for convenient explanation, and are not to be taken as limiting the scope of the technology. We claim all that is encompassed by the appended claims.

We claim:

1. An image generation method, comprising: receiving a fluorescent image of a specimen, wherein the specimen is fluorescently stained and a first beam has been selected to produce fluorescence by the fluorescent stain so that the first image is a fluorescence image of the specimen; receiving a refractive dark field image of the specimen, wherein a second stimulus beam has been applied to the specimen so that the second image is a refractive dark field image;
  applying a color mapping to the refractive dark field image to produce a pseudo-color dark field image;
  applying a color lookup table to the fluorescence image, and generating a converted fluorescent image wherein the color lookup table is associated with at least one absorptive stain;
  combining the pseudo-color dark field image and the converted fluorescence image and generating a refractive dark field and fluorescence combined image; and
  inverting the refractive dark field and fluorescence combined image to produce a brightfield rendered image.

2. The method of claim 1, further comprising recording the fluorescence image and the refractive dark field image as corresponding recorded images.

3. The method of claim 1, wherein the absorptive stain is an eosin stain.

4. The method of claim 1, wherein the fluorescence is based on DAPI fluorescence, and the color lookup table associated with the fluorescence image is based on a hematoxylin stain.

5. The method of claim 1, further comprising producing a pseudo-brightfield recorded image based on the refractive dark field and fluorescence combined recorded image.

6. The method of claim 5, further comprising applying color lookup tables to the refractive dark field image and the fluorescence image so as to produce an image having image contrast associated with hematoxylin and eosin staining.

7. The method of claim 1, further comprising generating a mass spectroscopic image of the specimen.

8. The imaging apparatus, comprising:
at least one image capture device that receives first and second images, wherein the first image is a refractive dark field image and the second image is a fluorescence image; and
an image processor coupled to the image capture device that applies a color lookup table to at least one of the first and second recorded images and generates a pseudo-colored rendering of at least one of the first and second images,
wherein the image processor combines the pseudo-colored rendering of at least one of the first and second images with the other of the at least one of the first and second images and generates a refractive dark field and fluorescence combined image, based on the pseudo-colored rendering of at least one of the first and second images,
wherein when image processer generates a pseudo-colored rendering of the first image, the image processor processes the first image based on a color lookup table associated with an eosin stain, and when the image processor generates a pseudo-colored rendering of the second image, the image processor processes the second image based on color lookup table associated with a hematoxylin stain, and
wherein the image processor inverts the refractive dark field and fluorescence combined image to produce a brightfield rendered image.

9. The imaging apparatus of claim 8, further comprising rendering the refractive dark field and fluorescence combined image as a pseudo-brightfield image.

10. The imaging apparatus of claim 8, wherein the image capture device is configured to receive the first image and the second image as side by side images.

11. The imaging apparatus of claim 8, wherein the image processor is configured to overlay the first and second images to produce the refractive dark field and fluorescence combined image.

12. The imaging apparatus of claim 8, further comprising a display configured to receive and display the refractive dark field and fluorescence combined image.

13. At least one non-transitory computer readable storage media comprising computer-executable instructions for:
receiving a first image and a second image associated with a common portion of a specimen section, wherein the first image is a refractive dark field image and the second image is a fluorescence image;
combining the refractive dark field image and the fluorescence image and generating a refractive dark field and fluorescence combined image, wherein before the refractive dark field image is combined with the fluorescence image, the refractive dark field image is processed based on a color lookup table associated with an eosin stain and the fluorescence image is processed based on color lookup table associated with a hematoxylin stain, and wherein the refractive dark field and fluorescence combined image is based on the processed first and second images;
inverting the refractive dark field and fluorescence combined image, and generating a pseudo-color brightfield hematoxylin and eosin image based on the processed first image and the processed second image.

14. The at least one computer readable storage media of claim 13, further comprising computer executable instructions for receiving a mass spectroscopic image of the common specimen section, and including the mass spectroscopic image in the refractive dark field and fluorescence combined image.

15. An image processor, comprising:
image inputs configured that receives a first image and a second image, wherein the first image is a refractive dark field image and the second image is a fluorescent image;
a color lookup table input that receives, a first color lookup table associated with an eosin stain and a second color lookup table associated with a hematoxylin stain;
an image combiner that processes the refractive dark field image based on the first color lookup table associated with an eosin stain and that processes the fluorescent image based on the second color lookup table associated with the eosin stain and produces a pseudo-color refractive dark field image and a pseudo-color fluorescent image, and combines the pseudo-color refractive dark field image with the pseudo-color fluorescent image and generates a combined refractive dark field and fluorescent image, and produces a brightfield image rendering based on the combined refractive dark field and fluorescent image after inverting the combined refractive dark field and fluorescent image.

* * * * *